(12) United States Patent
Flagan et al.

(10) Patent No.: US 8,597,577 B2
(45) Date of Patent: Dec. 3, 2013

(54) SWEPT-FREQUENCY SEMICONDUCTOR LASER COUPLED TO MICROFABRICATED BIOMOLECULAR SENSOR AND METHODS RELATED THERETO

(75) Inventors: Richard C. Flagan, Pasadena, CA (US);
Amnon Yariv, Pasadena, CA (US);
Jason Gamba, Pasadena, CA (US);
Naresh Satyan, Pasadena, CA (US);
Jacob Sendowski, Pasadena, CA (US);
Arseny Vasilyev, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 242 days.

(21) Appl. No.: 13/031,050

(22) Filed: Feb. 18, 2011

(65) Prior Publication Data

US 2012/0156802 A1    Jun. 21, 2012

Related U.S. Application Data

(60) Provisional application No. 61/306,379, filed on Feb. 19, 2010.

(51) Int. Cl.
| | |
|---|---|
| H01S 3/13 | (2006.01) |
| H01S 5/06 | (2006.01) |
| H01P 7/00 | (2006.01) |
| G01B 11/14 | (2006.01) |
| G01B 11/24 | (2006.01) |
| G01N 21/05 | (2006.01) |

(52) U.S. Cl.
USPC ...... 422/82.11; 422/502; 355/4.01; 355/5.01; 355/5.09; 355/237.4; 359/577; 359/578; 372/20; 372/28; 372/29.016; 372/29.023; 372/38.01; 372/38.02; 382/128; 382/129; 385/1; 435/6.1; 436/46; 436/63; 436/94; 436/96; 436/111; 436/164; 436/501; 438/48; 600/310; 600/473; 600/476

(58) Field of Classification Search
None
See application file for complete search history.

(56) References Cited

U.S. PATENT DOCUMENTS

| | | | |
|---|---|---|---|
| 3,589,794 | A | 6/1971 | Marcatili |
| 3,780,297 | A | 12/1973 | Geary |
| 3,913,126 | A | 10/1975 | Hooker et al. |
| 4,071,753 | A | 1/1978 | Fulenwider et al. |
| 4,132,959 | A | 1/1979 | Bouwhuis et al. |
| 4,282,499 | A | 8/1981 | DeFonzo |
| 4,419,895 | A | 12/1983 | Fuller |
| 4,695,121 | A | 9/1987 | Mahapatra et al. |

(Continued)

FOREIGN PATENT DOCUMENTS

| | | |
|---|---|---|
| FR | 2703473 | 10/1994 |
| GB | 2175437 | 11/1986 |
| JP | 5203826 | 8/1993 |
| WO | 98/05995 | 2/1998 |

OTHER PUBLICATIONS

Sannomiya, T., et al., In situ sensing of single binding events by localized surface plasmon resonance, Nano Letters 2008, 8: 3450-3455.

(Continued)

*Primary Examiner* — Sally Merkling
*Assistant Examiner* — Timothy G Kingan
(74) *Attorney, Agent, or Firm* — Steinfl & Bruno LLP

(57) ABSTRACT

An optoelectronic swept-frequency semiconductor laser coupled to a microfabricated optical biomolecular sensor with integrated resonator and waveguide and methods related thereto are described. Biomolecular sensors with optical resonator microfabricated with integrated waveguide operation can be in a microfluidic flow cell.

9 Claims, 7 Drawing Sheets

(56) References Cited

U.S. PATENT DOCUMENTS

| | | | |
|---|---|---|---|
| 5,343,490 | A | 8/1994 | McCall |
| 5,436,749 | A | 7/1995 | Pidgeon, Jr. et al. |
| 5,561,022 | A | 10/1996 | Nogami et al. |
| 5,717,708 | A | 2/1998 | Mells |
| 5,878,070 | A | 3/1999 | Ho et al. |
| 6,052,495 | A | 4/2000 | Little et al. |
| 6,078,605 | A | 6/2000 | Little et al. |
| 6,101,300 | A | 8/2000 | Fan et al. |
| 6,222,964 | B1 | 4/2001 | Sadot et al. |
| 6,259,717 | B1 | 7/2001 | Stone et al. |
| 6,359,917 | B1 | 3/2002 | Cutler et al. |
| 6,560,253 | B1 | 5/2003 | Munks et al. |
| 6,583,399 | B1 | 6/2003 | Hunziker et al. |
| 6,901,101 | B2 | 5/2005 | Frick |
| 7,324,569 | B2 | 1/2008 | Flanders et al. |
| 7,492,795 | B1 | 2/2009 | Delfyett et al. |
| 7,545,843 | B2 | 6/2009 | Armani et al. |
| 7,781,217 | B2 | 8/2010 | Armani et al. |
| 2001/0033587 | A1 | 10/2001 | Painter et al. |
| 2002/0018611 | A1 | 2/2002 | Maleki et al. |
| 2003/0021518 | A1 | 1/2003 | Smirnov et al. |
| 2004/0179573 | A1 | 9/2004 | Armani et al. |
| 2005/0163185 | A1 | 7/2005 | Vahala et al. |
| 2006/0062523 | A1 | 3/2006 | Guo et al. |
| 2006/0239312 | A1 | 10/2006 | Kewitsch et al. |
| 2006/0245456 | A1 | 11/2006 | Lasri et al. |
| 2007/0183465 | A1 | 8/2007 | Mullane et al. |

OTHER PUBLICATIONS

Vollmer, F., et al., Whispering-gallery-mode biosensing: Label-free detection down to single molecules, Nature Methods 2008, 5: 591-596.
Qavi, A., et al., Label-free technologies for quantitative multiparameter biological analysis, Anal. Bioanal. Chem. 2009, 394: 121-135.
Vollmer, F., et al., Single virus detection from reactive shift of a whispering-gallery mode, PNAS 2008, 105: 20701-20704.
Ramachandran, A., et al., A universal biosensing platform based on optical micro-ring resonators, Biosensors and Bioelectronics 2008, 23: 939-944.
Armani, A., et al., Label-free, single-molecule detection with optical microcavities, Science 2007, 317: 783-787.
Nogueira, L., et al., Prostatic specific antigen for prostate cancer detection, International Braz. J. Urol. 2009, 35: 521-531.
Satyan, N., et al., Precise control of broadband frequency chirps using optoelectronic feedback, Optics Express 2009, 17: 15991-15999.
Matsko, A., et al., Optical resonators with whispering gallery modes—part I: basics, IEEE Journal of Selected Topics in Quantum Electronics 2006, 12: 3-14.
Ilchenko, V., et al., Optical resonators with whispering gallery modes—part II: applications, IEEE Journal of Selected Topics in Quantum Electronics 2006, 12: 15-32.
Vollmer, F., et al., Protein detection by optical shift of a resonant microcavity, Applied Physics Letters 2002, 80: 4057-4059.
Grudinin, I., et al., Ultrahigh optical Q factors of crystalline resonators in the linear regime, Physical Review A 2006, 74: 063806-1-063806-9.
Fan, X., et al., Sensitive optical biosensors for unlabeled targets: a review, Analytica Chimica Acta 2008, 620: 8-26.
Hale, G., et al., Optical constants of water in the 200-nm to 200-μm wavelength, Applied Optics 1973, 12: 555-563.
Pang, L., et al., Spectral sensitivity of two-dimensional nanohole array surface plasmon polariton resonance sensor, Applied Physics Letters 2007, 91: 123112-1-123112-3.
Vasilyev, A., et al., Multiple source frequency-modulated continuous-wave optical reflectometry: theory and experiment, Applied Optics 2010, 49: 1932-1937.
Satyan, N., et al., Chirp multiplication by four wave mixing for wideband swept-frequency sources for high resolution imaging, Journal of Lightwave Technology 2010, 28: 2077-2083.
Armani, A., et al., Heavy water detection using ultra-high-Q microcavities, Optics Letters 2006, 31: 1896-1898.
Kalia, J., et al., Advances in bioconjugation, Current Organics Chemistry 2010, 14: 138-147.
Harder, P., et al., Molecular confirmation in oligo(ethyleneglycol)-terminated self-assembled monolayers on gold and silver surfaces determines their ability to resist protein adsorption, J. Phys. Chem. B 1998, 102: 426-436.
Ostuni, E., et al., A survey of structure—property relationships of surfaces that resist the adsorption of protein, Langmuir 2001, 17: 5605-5620.
Schlossbauer, A., et al., Click chemistry for high-density biofunctionalization of mesoporous silica, JACS 2008, 130: 12558-12559.
Sun, X., et al., Carbohydrate and protein immobilization onto solid surfaces by sequential diels—alder and azide—alkyne cycloadditions, Bioconjugate Chemistry 2006, 17: 52-57.
Tombelli, S., et al., Analytical applications of aptamers, Biosensors and Bioelectronics 2005, 20: 2424-2434.
Almeida, V., et al., Nanotaper for compact mode conversion, Optics Letters 2003, 28: 1302-1304.
McNab, S., et al., Ultra-low loss photonic integrated circuit with membrane-type photonic crystal wavguides, Optical Society of America 2003, 11: 2927-2939.
Sun, X., et al., Adiabaticity criterion and the shortest adiabatic mode transformer in a coupled-waveguide system, Optics Letters 2009, 34: 280-282.
PCT International Preliminary Report on Patentability completed on May 16, 2009 for PCT Application No. PCT/US2003/031727 filed on Oct. 2, 2003 in the name of California Institue of Technolgy.
PCT International Search Report mailed on Mar. 26, 2005 for PCT Application No. PCT/US2003/031727 filed on Oct. 2, 2003 in the name of California Institue of Technolgy.
PCT International Search Report mailed on Nov. 14, 2011 for PCT Application No. PCT/US2011/025504 filed on Feb. 18, 2011 in the name of California Institue of Technolgy et al.
PCT Written Opinion mailed on Nov. 14, 2011 for PCT Application No. PCT/US2011/025504 filed on Feb. 18, 2011 in the name of California Institue of Technolgy et al.
Non-Final Office Action mailed on Oct. 13, 2005 for U.S. Appl. No. 10/678,354, filed Oct. 2, 2003 in the name of Deniz K. Armani et al.
Restriction Requirement mailed on Jan. 28, 2011 for U.S. Appl. No. 12/540,643, filed Aug. 13, 2009 in the name of George Rakuljic et al.
Notice of Allowance mailed on Jan. 11, 2012 for U.S. Appl. No. 12/540,643, filed Aug. 13, 2009 in the name of George Rakuljic et al.
Non-Final Office Action mailed on May 25, 2011 for U.S. Appl. No. 12/540,643, filed Aug. 13, 2009 in the name of George Rakuljic et al.
Non-Final Office Action mailed on Apr. 30, 2007 for U.S. Appl. No. 10/678,354, filed Oct. 2, 2003 in the name of Deniz K. Armani et al.
Final Office Action mailed on Oct. 19, 2007 for U.S. Appl. No. 10/678,354, filed Oct. 2, 2003 in the name of Deniz K. Armani et al.
Final Office Action mailed on Feb. 12, 2007 for U.S. Appl. No. 10/678,354, filed Oct. 2, 2003 in the name of Deniz K. Armani et al.
EP Communication mailed on Jul. 29, 2005 for European Application No. 03816213.7 filed on in the name of California Institue of Technolgy.
EP Communication mailed on Jul. 13, 2006 for European Application No. 03816213.7 filed on in the name of California Institue of Technolgy.
EP Communication 51(4) mailed on Mar. 19, 2007 for European Application No. 03816213.7-2216 filed on in the name of California Institue of Technolgy.
Amman, M-C., et al., Laser ranging: a critical review of usual techniques for distance measurement, Opt. Eng. 2001, 40: 10-19.
Armani, A.M., et al., Label-free, single-molecule detection with optical microcavities, Science 2007, 317: 783-786.
Armani, AM, et al., Ultra-high-Q microcavity operation in $H_2O$ and $D_2O$, Appl. Phys. Letters 2005, 87: 151118-1-151118-3.
Armani, AM., et al., Chemical and Biological Detectors using Ultra-High-Q Microresonators, Proc. of SPIE 2006, 6376: 637606-1-637606-10.
Aramni, AM, et al., Heavy water detection using ultra-high-$Q$ microcavities, Opt. Letters 2006, 31: 1896-1898.

(56) References Cited

OTHER PUBLICATIONS

Armani, DK, et al., Ultra-high-Q toroid microcavity on a chip, *Nature* 2003, 421: 925-928.
Armani, AM, et al., Biological and Chemical Detection using Ultra-high-Q Toriodal Microresonators, pp. 1-22, Biophysical Society Annual Meeting, 2007.
Bahreini, R., et al., Measurements of Secondary Organic Aerosol from Oxidation of Cycloalkenes, Terpenes, and *m*-Xylene Using an Aerodyne Aerosol Mass Spectrometer, *Environ. Sci. & Techno.* 2005, 39: 5674-5688.
Beheim, G., et al., Remote displacement measurements using a laser diode, *Electronic Letters* 1985, 21: 93-94.
Min, B., et al., Compact, fiber-compatible, cascaded Raman laser, *Opt. Letters* 2003, 28: 1507-1509.
Burdic, WS, et al., Radar Signal Analysis 1968, Chap. 5, pp. 158-223.
Burrows, E.C., et al., High resolution laser lidar utilizing two-section distributed feedback semiconductor laser as a coherent source, *Electronics Letters* 1990, 26: 577-579.
Cai, M., et al., Fiber-coupled microsphere laser, *Opt. Letters* 2000, 25: 1430-1432.
Cai, M., et al., Observation of Critical Coupling in a Fiber Taper to a Silica-Microsphere Whispering-Gallery Mode System, *Phys. Review Letters* 2000, 85: 74-77.
Chan, I., et al., Gas Phase Pulse Etching of Silicon for MEMS With Xenon Difluoride, Proc. of the 1999 *IEEE Canadian Conf. on Elec. & Comp. Engineering*, May 9-12, 1999 pp. 1637-1642.
Chong, C., et al., Spectral narrowing effect by quasi-phase continuous tuning in high-speed wavelength-swept light source, *Opt. Express* 2008, 16: 21105-21118.
Chu, S., et al., An Eight-Channel Add-Drop Filter Using Vertically Coupled Microring Resonators over a Cross Grid, *IEEE Photonics Tech. Letters* 1999, 11: 691-693.
Chu, D.Y., et al., Observation of enhanced photoluminescence in erbium-doped semiconductor microdisk resonator, *Appl. Phys. Letters* 1995, 66: 2843-2845.
Dieckmann, A., FMCW-LIDAR with tunable twin-guide laser diode, *Electronics Letters* 1994, 30: 308-309.
Djordjev, K., et al., Microdisk Tunable Resonant Filters and Switches, *IEEE Photo. Tech. Letters* 2002, 14: 828-830.
Djordjev, K., et al., Vertically Coupled InP Microdisk Switching Devices With Electroabsorptive Active Regions, *IEEE Photo. Tech. Letters* 2002, 14: 1115-1117.
Fang, A., et al., Electrically pumped hybrid AlGaInAs-silicon evanescent laser, *Optics Express* 2006, 14: 9203-9210.
Fehsenfeld, FC, et al., International Consortium for Atmospheric Research on Transport and Transformation (ICARTT): North America to Europe—Overview of the 2004 summer field study, *J. Geophys. Research* 2006, 111: D23S01-1-D23801-36.
Flagan, RC, et al., A thermodynamically consistent kinetic framework for binary nucleation, *The J. Chem. Phys.* 2007, 127: 214503-1-214503-7.
Fountoukis, C., et al., Aerosol-cloud drop concentration closure for clouds sampled during the International Consortium for Atmospheric Research on Transport and Transformation 2004 campaign, *J. Geophys. Research* 2007, 112: D10S30-1-D10S30-12.
Fritsch, K., et al., Remote displacement measurements using a laser diode, *Elec. Letters* 1985, 21: 93-94.
Gayral, B., et al., High-Q wet-etched GaAs microdisks containing InAs quantum boxes, *Appl. Phys. Letters* 1999, 75: 1908-1910.
Gerard., JM, et al., Quantum boxes as active probes for photonic microstructures: The pillar microcavity case, *App. Phys. Letters* 1996; 69: 449-451.
Goodrich, T., et al., Direct Detection of Genomic DNA by Enzymatically Amplified SPR Imaging Measurements of RNA Microarrays, *JACS* 2004, 126: 4086-4087.
Gora, M., et al., Ultra high-speed swept source OCT imaging of the anterior segment of human eye at 200 kHz with adjustable imaging range, *Optics Express* 2009, 17: 14880-14894.
Gorodetsky, ML, et al., Ultimate Q of optical microsphere resonators, *Optics Letters* 1996, 21: 453-455.
Grover, R., et al., Parallel-Cascaded Semiconductor Microring Resonators for High-Order and Wide-FSR Filters, *J. of Lightwave Technology* 2002, 20: 900-905.
Grover, R., et al., Parallel-Cascaded Semiconductor Microring Resonators for High-Order and Wide-FSR Filters, *J Lightwave Technology* 2002, 20: 900-905.
Hale, G., et al., Optical Constants of Water in the 200-nm to 200-µm Wavelength Region, *Applied Optics* 1973, 12: 555-563.
Harder, P., et al., Molecular conformation in oligo(ethyleneglycol)-terminated self-assembled monolayers on gold and silver surfaces determines their ability to resist protein adsorption, J. Phys. Chem. B 1998, 102: 426-436.
Heald, C., et al., A large organic aerosol source in the free troposphere missing from current models, *Geophys. Res. Letters* 2005, 32: L18809-1-L18809-4.
Huang, D., et al., Optical Coherence Tomography, *Science* 1991, 254: 1178-1181.
Huber, R., et al., Fourier domain mode locking (FDML): A new laser operating regime and applications for optical coherence tomography, *Optics Express* 2006, 14: 3225-3237.
Iiyama, K., et al., Linearizing optical frequency-sweep of a laser diode for FMCW reflectometry, *J. Lightwave Tech.* 1996, 14: 173-178.
Kawachi, M., et al., Silica waveguides on silicon and their application to integrated-optic components, *Optical and Quantum Elec.* 1990, 22: 391-416.
Kippenberg, TJ, et al., Fabrication and coupling to planar high-Q silica disk microcavities, *Appl. Phys. Letters* 2003, 83: 797-799.
Kleppner, D., et al., Inhibited Spontaneous Emission, *Phys. Rev. Letters* 1981, 47: 233-236.
Knight, JC, et al., Phase-matched excitation of whispering-gallery-mode resonances by a fiber taper, *Optics Letters* 1997, 22: 1129-1131.
Krioukov, E., et al., Sensor based on an integrated optical microcavity, *Optics Letters* 2002, 27: 512-514.
Little, BE, et al., Wavelength Switching and Routing Using Absorption and Resonance, *IEEE Photo. Tech. Letters* 1998, 10: 816-818.
Little, BE, et al., Vertically Coupled Glass Microring Resonator Channel Dropping Filters, *IEEE Photo. Tech. Letters* 1999, 11: 215-217.
Little, BE, et al.., Microring Resonator Channel Dropping Filters, *J. Lightwave Tech.* 1997, 15: 998-1005.
Lu, ML, et al., The Marine Stratus/Stratocumulus Experiment (MASE): Aerosol-cloud relationships in marine stratocumulus, *J. Geophysical Res.* 2007, 112: D10209-1-D10209-21.
McCall, SL, et al., Whispering-gallery mode microdisk lasers, *Appl. Phys. Letters* 1992, 60: 289-291.
McNab, S., et al., Ultra-low loss photonic integrated circuit with membrane-type photonic crystal waveguides, *Optics Express* 2003, 11: 2927-2939.
Michler, P., et al., Quantum Dot Lasers Using High-Q Microdisk Cavities, *Phys. Statt. Sol.* 2001, 224: 797-801.
Offrein, BJ, et al., Resonant Coupler-Based Tunable Add-After-Drop Filter in Silicon-Oxynitride Technology for WDM Networks, *IEEE J. of Selected Topics in Quant. Elec.* 1999, 5: 1400-1406.
Rabiei, P., Polymer Micro-Ring Filters and Modulators, *J. of Lightwave Technology* 2002, 20: 1968-1975.
Rissman, TA, et al., CCN behavior of organic aerosol particles, *Atmos. Chem. Phys.* 2007, 7: 2949-2971.
Roos, PA, et al., Ultrabroadband optical chirp linearization for precision metrology applications, *Optics Letters* 2009, 34: 3692-3694.
Sandoghdar, V., et al., Very low threshold whispering-gallery-mode microsphere laser, *Phys. Rev. A* 1996, 54: R1777-R1780.
Satyan, N. et al., "Coherent Power Combination of Semiconductor Lasers using Optical Phase-Lock Loops," *IEEE J. of Sel. Top. in Quantum Electron.* 15, 240-247 (2009).
Satyan, N. et al., "Phase- Controlled Apertures Using Heterodyne Optical Phase-Locked Loops," *IEEE Photon. Tech. Lett.* 20, 897-899 (2008).
Satyan, N., et al., Coherence Cloning Using Semiconductor Laser Optical Phase-Lock Loops, *IEEE J. of Quan. Elec.* 2009, 45: 755-761.

(56) References Cited

OTHER PUBLICATIONS

Schiller, S., et al., Fused-silica monolithic total-internal-reflection resonator, *Optics Letters* 1992, 17: 378-380.
Shearn, M., et al., Advanced silicon processing for active planar photonic devices, *J. Vac. Sci. Technol. B* 2009, 27: 3180-3182.
Soref, R., et al., Proposed N-Wavelength M-Fiber WDM Crossconnect Switch Using Active Microring Resonators, *IEEE Photo. Tech. Letters* 1998, 10: 1121-1123.
Sorooshian, A., et al., Modeling and Characterization of a Particle-into-Liquid Sampler (PILS), *Aerosol Sci. and Tech.* 2006, 40: 396-409.
Sorooshian, A., et al., Oxalic acid in clear and cloudy atmospheres: Analysis of data from International Consortium for Atmospheric Research on Transport and Transformation 2004, *J. of Geophys. Res.* 2006, 111: D23S45-1-D23S45-17.
Spillane, SM, et al., Ultralow-threshold Raman laser using a spherical dielectric microcavity, *Letters to Nature* 2002, 415: 621-623.
Stern, E., et al., Label-free immunodetection with CMOS-compatible semiconducting nanowires, *Nature* 2007, 445: 519-522, Supplemental Information pp. 1-18.
Strzelecki, EM. et al., Investigation of Tunable Single Frequency Diode Lasers for Sensor Application, *J. Lightwave Technology* 1988, 6: 1610-1618.
Sun, X., et al., Adiabaticity criterion and the shortest adiabatic mode transformer in a coupled-waveguide system, *Optics Letters* 2009, 34:280-282.
Sun, X., et al., Electrically pumped hybrid evanescent Si/InGaAsP lasers, *Optics Letters* 2009, 34: 1345-1347.
Sun, X., et al., Engineering supermode silicon/III-V hybrid waveguides for laser oscillation, *J. Opt. Soc. Am. B*. 2008, 25: 923-926.
Sun, X., et al., Electrically Pumped Supermode Si/InGaAsP Hybrid Lasers, *IEEE* 2010, pp. 1-2.
Vahala, K., et al., Biological Detectors using Ultra-High-Q Microresonators, *IEEE* 2006, pp. 50-51.
Vahala, K., et al., Photonic clocks, Raman lasers, and Biosensors on Silicon, *IEEE* 2006, pp. 40-41.
Vollmer, F., et al., Single virus detection from the reactive shift of a whispering-gallery mode, *PNAS* 2008, 105: 20701-20704.
von Klitzing, W., et al., Tunable whispering gallery modes for spectroscopy and CQED experiments, *New Journal of Physics* 2001, 3: 14-1-14-14.
Yanagase, Y., et al., Box-Like Filter Response and Expansion of FSR by a Vertically Triple Coupled Microring Resonator Filter, *J. of Lightwave Technology* 2002, 20: 1525-1529.
Yang, L., et al., Gain functionalization of silica microresonators, *Optics Letters* 2003, 28: 592-594.
Yariv, A., Universal relations for coupling of optical power between microresonators and dielectric waveguides, *Electronic Letters* 2000, 36: 321-322.
Yariv, A., Critical Coupling and Its Control in Optical Waveguide-Ring Resonator Systems, *IEEE Photo. Tech. Letters* 2002, 14: 483-485.
Yariv, A., et al., Dynamic analysis of the semiconductor laser as a current-controlled oscillator in the optical phased-lock loop: applications, *Optics Letters* 2005, 30: 2191-2193.
Yariv, A., et al., Supermode Si/III-V hybrid lasers, optical amplifiers and modulators: A proposal and Analysis, *Optics Express* 2007, 15: 9147-9151.
Yun, SH, et al., High-speed optical frequency-domain imaging, *Optics Express* 2003, 11: 2953-2963.
Yun, SH, et al., High-speed wavelength-swept semiconductor laser with a polygon-scanner-based wavelength filter, *Optics Letters* 2003, 28: 1981-1983.
Zheng, J., Analysis of optical frequency-modulated continuous-wave interference, *Applied Optics* 2004, 43: 4189-4198.
Zheng, G., et al., Multiplexed electrical detection of cancer markers with nanowire sensor arrays, *Nat. Biotech.* 2005, 23: 1294-1301.
Final Office Action mailed on October, 19, 2007 for U.S. Appl. No. 10/678,354, filed Oct. 2, 2003 in the name of Deniz K. Armani et al.

Almeida, V. et al., Nanotaper for Compact Mode Conversion, *Optics Letters* 2003, 28:1302-1304.
Armani, A.M. et al., Label-free, single-molecule detection with optical microcavities, *Science* 2007, 317: 783-786.
Armani, AM, et al., Biological and Chemical Detection using Ultra-high-Q Toriodal Microresonators, pp. 1-22.
Bahreini, R., et al., Measurements of Secondary Organic Aerosol from Oxidation of Cycloalkenes, Terpenes, and m-Xylene Using an Aerodyne Aerosol Mass Spectrometer, *Environ. Sci. & Technol.* 2005, 39: 5674-5688.
Beheim, G., et al., Remote displacement measurements using a laser diode, *Electronic Letters* 1985, 21:93-94.
Burdic, W.S., et al., Radar Signal Analysis 1968, Chap. 5, pp. 158-223.
Dieckmann, A., FMCW-LIDAR with tunable twin-guide laser diode, *Electronics Letters*, 1994, 30: 308-309.
Djordjev, K., et al., Microdisk Tunable Resonant Filters and Switches, *IEEE Photo. Tech. Letters*, 2002, 14: 828-830.
Djordjev, K., et al., Vertically Coupled InP Microdisk Switching Devices With Electroabsorptive Active Regions, *IEEE Photo. Tech. Letters*, 2002, 14: 1115-1117.
Fan, X., et al., Sensitive optical biosensors for unlabeled targets: a review, *Analytica Chimica Acta*, 2008, 620: 8-26.
Fang, A., et al., Electrically pumped hybrid AlGaInAs-silicon evanescent laser, *Optics Express*, 2006, 14: 9203-9210.
Fehsenfeld, F.C, et al., International Consortium for Atmospheric Research on Transport and Transformation (ICARTT): North America to Europe—Overview of the 2004 summer field study, *J. Geophys. Research*, 2006, 111: D23S01-1-D23S01-36.
Flagan, R.C, et al., A thermodynamically consistent kinetic framework for binary nucleation, *The J. Chem. Phys.* 2007, 127: 214503-1-214503-7.
Fountoukis, C., et al., Aerosol-cloud drop concentration closure for clouds sampled during the International Consortium for Atmospheric Research on Transport and Transformation 2004 campaign, *J. Geophys. Research*, 2007, 112: D10S30-1-DI0S30-12.
Fritsch, K., et al., Remote displacement measurements using a laser diode, *Elec. Letters*, 1985, 21: 93-94.
Gayral, B., et al., High-Q wet-etched GaAs microdisks containing InAs quantum boxes, *Appl. Phys. Letters*, 1999, 75: 1908-1910.
Gerard., JM, et al., Quantum boxes as active probes for photonic microstructures: The pillar microcavity case, *App. Phys. Letters* 1996, 69: 449-451.
Goodrich, T., et al., Direct Detection of Genomic DNA by Enzymatically Amplified SPR Imaging Measurements of RNA Mictoarrays, *JACS* 2004, 126: 4086-4087.
Gora, M., et al., Ultra high-speed swept source OCT imaging of the anterior segment of human eye at 200 kHz with adjustable imaging range, *Optics Express* 2009; 17: 14880-14894.
Grover, R. et al., Parallel-Cascaded Semiconductor Microring Resonators for High-Order and Wide-FSR Filters, *J. of Lightwave Technology*, 2002, 20: 900-905.
Hale, G., et al., Optical Constants of Water in the 200-nm to 200 μm Wavelength Region, *Applied Optics*, 1973, 12:555-563.
Harder, P., et al., Molecular Conformation in oligo(ethyleneglycol)-terminated self-assembled monolayers on gold and silver surfaces determines their ability to resist protein adsorption, *J. Phys. Chem. B*. 1998, 102:426-436.
Heald, C., et al., A large organic aerosol source in the free troposphere missing from current models, *Geophys. Res. Letters*, 2005, 32: L18809-1-L18809-4.
Iiyama, K., et al., Linearizing optical frequency-sweep of a laser diode for FMCW reflectometry, *J Lightwave Tech.* 1996, 14: 173-178.
Ilchenko, V., et al., Optical Resonators with Whispering Gallery Modes—Part II: Applications *IEEE Jounral of Selected Topics in Quantum Eletronics* 2006, 14:15-32.
Kalia, J., et al., Advances in Bioconjugation, *Current Organics Chemistry*, 2010, 14:138-147.
Kawachi, M., et al., Silica waveguides on silicon and their application to integrated-optic components, *Optical and Quantum Elec.*, 1990, 22: 391-416.

(56) References Cited

OTHER PUBLICATIONS

Kippenberg, TJ, et al., Fabrication and coupling to planar high-Q silica disk microcavities, *Appl. Phys. Letters*, 2003, 83: 797-799.

Kleppner, D., et al., Inhibited Spontaneous Emission, *Phys. Rev. Letters*, 1981, 47: 233-236.

Knight, JC, et al., Phase-matched excitation of whispering-gallery-mode resonances by a fiber taper, *Optics Letters*, 1997, 22: 1129-1131.

Little, BE, et al., Vertically Coupled Glass Microring Resonator Channel Dropping Filters, *IEEE Photo. Tech. Letters*, 1999, 11: 215-217.

Little, BE, et al.., Microring Resonator Channel Dropping Filters, *J. Lightwave Tech.*, 1997, 15: 998-1005.

Lu, ML, et al., The Marine Stratus/Stratocumulus Experiment (MASE): Aerosol-cloud relationships in marine stratocumulus, *J. Geophysical Res.*, 2007, 112: D10209-1-D10209-21.

Matsko, A., et al., Optical resonators with whispering gallery modes—part I: basics, *IEEE Journal of Selected Topics in Quantum Electronics*, 2006, 12: 3-14.

McCall, SL, et al., Whispering-gallery mode microdisk lasers, *Appl. Phys. Letters*, 1992, 60: 289-291.

McNab, S.L., Ultra-low loss photonic integrated with membrane-type photonic crystal waveguides, *Optics Express*, 2003, 1:1 22; pp. 2927-2939.

Michler, P., et al., Quantum Dot Lasers Using High-Q Microdisk Cavities, *Phys. Stat. Sol.*, 2001, 224: 797-801.

Nogueira, L., et al., Prostatic Specific antigen for prostate cancer detection, *International Braz. J. Urol.*, 2009, 35:521-531.

Offrein, BJ, et al., Resonant Coupler-Based Tunable Add-After-Drop Filter in Silicon—Oxynitride Technology for WDM Networks, *IEEE J. of Selected Topics in Quant. Elec.*, 1999, 5: 1400-1406.

Ostuni, E., et al., A survey of structure-property relationships of surfaces that resist the adsorption of protein, *Langmuir*, 2001, 17:5605-5620.

Pang, L., et al., Spectral sensitivity of two-dimensional nanohole array surface plasmin polariton resonance sensor, *Applied Physics Letters*, 2007, 91:123112-1-123112-3.

Qavi, A., et al., Label-free technologies for quantitative multiparameter biological analysis, *Anal. Bioanal. Chem.*, 2009, 394:121-135.

Rabiei, P., Polymer Micro-Ring Filters and Modulators, *J. of Lightwave Technology*, 2002, 20: 1968-1975.

Ramachandran, A., et al., A universal biosensing platform based on optical micro-ring resonators, *Biosensors and Bioelectronics*, 2008, 23: 939-944.

Rissman, TA, et al., CCN behavior of organic aerosol particles, *Atmos. Chem. Phys.*, 2007, 7: 2949-2971.

Roos, PA, et al., Ultrabroadband optical chirp linearization for precision metrology applications, *Optics Letters*, 2009, 34: 3692-3694.

Sandoghdar, V., et al., Very low threshold whispering-gallery-mode microsphere laser, *Phys. Rev. A*, 1996, 54: R1777-R1780.

Sannomiya, T., et al., In situ sensing of single binding events by localized surface plasmon resonance, *Nano Letters*, 2008, 8: 3450-3455.

Satyan, N., et al., Chirp multiplication by four wave mixing for wideband swept-frequency sources for high resolution imaging, *Journal of Lightwave Technology*, 2010, 28: 2077-2083.

N. Satyan, et al., "Coherent Power Combination of Semiconductor Lasers using Optical Phase-Lock Loops," *IEEE J. of Sel. Top. Quantum. Electron.*, 15,240-247 (2009).

N. Satyan, et al., "Phase-Controlled Apertures Using Heterodyne Optical Phase-Locked Loops," *IEEE Photon. Tech. Lett.*, 20, 897-899 (2008).

Satyan, N., et al., Precise control of broadband frequency chirps using optoelectronic feedback, *Optics Expres,s* 2009, 17: 15991-15999.

Satyan, N., et al., Coherence Cloning Using Semiconductor Laser Optical Phase-Lock Loops, *IEEE J. of Quan. Elec.*, 2009, 45: 755-761.

Schiller, S., et al., Fused-silica monolithic total-internal-reflection resonator, *Optics Letters*, 1992, 17: 378-380.

Schlossbauer, A., et al., Click chemistry for high-density biofunctionalization of mesoporous silica, *JACS*, 2008, 130: 12558-12559.

Shearn, M., et al., Advanced silicon processing for active planar photonic devices, *J. Vac. Sci. Technol. B*, 2009, 27: 3180-3182.

Soref, R., et al., Proposed $N$-Wavelength $M$-Fiber WDM Crossconnect Switch Using Active Microring Resonators, *IEEE Photo. Tech. Letters*, 1998, 10: 1121-1123.

Sorooshian, A., et al., Modeling and Characterization of a Particle-into-Liquid Sampler (PILS), *Aerosol Sci. and Tech.*, 2006, 40: 396-409.

Sorooshian, A., et al., Oxalic acid in clear and cloudy atmospheres: Analysis of data from International Consortium for Atmospheric Research on Transport and Transformation 2004, *J. of Geophys. Res.*, 2006, 111: D23S45-1-D23S45-17.

Spillane, SM, et al., Ultralow-threshold Raman laser using a spherical dielectric micro cavity, *Letters Nature*, 2002, 415: 621-623.

Stern, E., et al., Label-free immunodetection with CMOS-compatible semiconducting nanowires, *Nature*, 2007, 445: 519-522, & Supplementary Information pp. 1-18.

Strzelecki, EM. et al., Investigation of Tunable Single Frequency Diode Lasers for Sensor Application, *J. Lightwave Technology*, 1988, 6: 1610-1618.

Sun, X., et al., Adiabaticity criterion and the shortest adiabatic mode transformer in a coupled-waveguide system, *Optics Letters*, 2009, 34: 280-282.

Sun, X., et al., Carbohydrate and protein immobilization onto solid surfaces by sequential diels—alder and azide—alkyne cycloadditions, *Bioconjugate Chemistry*, 2006, 17: 52-57.

Sun, X., et al., Electrically pumped hybrid evanescent Si/InGaAsP lasers, *Optics Letters*, 2009, 34: 1345-1347.

Sun, X., et al., Engineering supermode silicon/III-V hybrid waveguides for laser oscillation, *J. Opt. Soc. Am. B.*, 2008, 25: 923-926.

Sun, X., et al., Electrically Pumped Supermode Si/InGaAsP Hybrid Lasers, *IEEE*, 2010, pp. 1-2.

Tombelli, S., et al., Analytical applications of aptamers, *Biosensors and Bioelectronics*, 2005; 20: 2424-2434.

Vahala, K., et al., Biological Detectors using Ultra-High-Q Microresonators, *IEEE*, 2006, pp. 50-51.

Vahala, K., et al., Photonic clocks, Raman lasers, and Biosensors on Silicon, *IEEE*, 2006, pp. 40-41.

Vasilyev, A., et al., Multiple Source frequency-modulated continuous-wave optical reflectometry: theory and experiment, *Applied Optics*, 2010, 49:1932-1937.

Vollmer, F., et al., Protein detection by optical shift of a resonant microcavity, *Applied Physics Letters*, 2002, 80: 4057-4059.

Vollmer, F., et al., Single Virus detection from the reactive shift of a whispering-gallery mode *PNAS*, 2008, 105:20701-20704.

Vollmer, F., et al., Whispering gallery-mode biosensing: Label-free detection down to single molecules *Nature Methods*, 2008, 5:591-596.

Yanagase, Y., et al., Box-Like Filter Response and Expansion of FSR by a Vertically Triple Coupled Microring Resonator Filter. *J. of Lightwave Technology*, 2002, 20: 1525-1529.

Yang, L. et al., Gain functionalization of silica microresonators, *Optics Letters*, 2003, 28: 592-594.

Yariv, A., Universal relations for coupling of optical power between microresonators and dielectric waveguides, *Electronic Letters*, 2000, 36: 321-322.

Yariv, A., Critical Coupling and Its Control in Optical Waveguide-Ring Resonator Systems, *IEEE Photo. Tech. Letters*, 2002, 14: 483-485.

(56) References Cited

OTHER PUBLICATIONS

Yariv, A., et al., Dynamic analysis of the semiconductor laser as a current-controlled oscillator in the optical phased-lock loop: applications, *Optics Letters*, 2005, 30: 2191-2193.

Yariv, A., et al., Supermode Si/III-V hybrid lasers, optical amplifiers and modulators: A proposal and Analysis, *Optics Express*, 2007, 15: 9147-9151.

Yun, S. H, et al., High-speed optical frequency-domain imaging, *Optics Express*, 2003, 11: 2953-2963.

Yun, S. H, et al., High-speed wavelength-swept semiconductor laser with a polygon-scanner-based wavelength filter, *Optics Letters*, 2003, 28: 1981-1983.

Zheng, J., Analysis of optical frequency-modulated continuous-wave interference, *Applied Optics*, 2004, 43: 4189-4198.

Zheng, G., et al., Multiplexed electrical detection of cancer markers with nanowire sensor arrays, 2005, 23: 1294-1301.

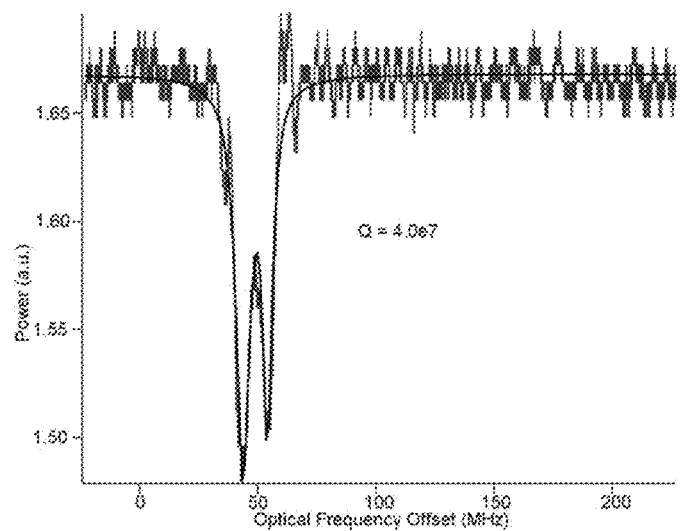
FIG. 4
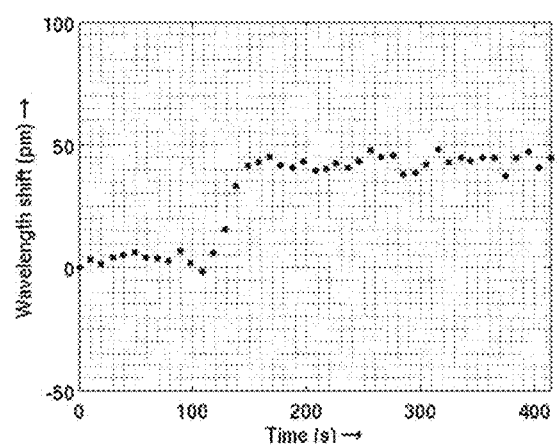
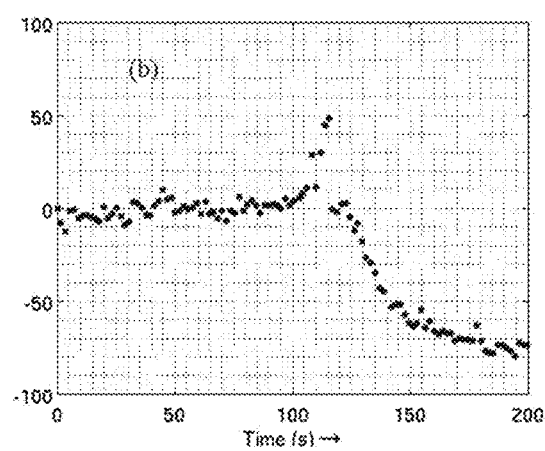
FIG. 5A
FIG. 5B

SWEPT-FREQUENCY SEMICONDUCTOR LASER COUPLED TO MICROFABRICATED BIOMOLECULAR SENSOR AND METHODS RELATED THERETO

CROSS REFERENCE TO RELATED APPLICATIONS

The present application claims priority to U.S. Provisional Application No. 61/306,379 entitled "Swept Frequency Semiconductor Laser Coupled to High-Q Optical Resonators for High Sensitivity Biomolecule Detection," filed on Feb. 19, 2010, which is incorporated herein by reference in its entirety. The present application may be related to U.S. patent application Ser. No. 12/540,643 entitled "Arbitrary Optical Waveform Generation Utilizing Optical Phase-Locked Loops," filed on Aug. 13, 2009, which is incorporated herein by reference in its entirety. The present application may also be related to U.S. Pat. No. 7,781,217 entitled "Biological and Chemical Microcavity Resonant Sensors and Methods of Detecting Molecules," and U.S. Pat. No. 7,545,843 entitled "Ultra-high Q Micro-resonator and Method of Fabrication," the disclosures of which are also incorporated herein by reference in their entirety.

STATEMENT OF GOVERNMENT GRANT

The invention described herein was made with U.S. Government support under Grant No. HR0011-10-C-0064 awarded by DARPA. The U.S. Government has certain rights in the invention.

FIELD

The present disclosure relates to molecular sensors. In particular, it relates to a swept-frequency semiconductor laser coupled to a microfabricated optical biomolecular sensor and methods related thereto.

BACKGROUND

Label-free biomolecular sensing using high quality factor (Q) optical resonators has the potential to achieve useful levels of sensitivity and may enable medical diagnostic tools which can be reliable and efficient.

Traditional biomolecular assays, which are an integral part of medical diagnostics, tend to be labor-intensive and time-consuming laboratory procedures. Various modern technologies and methods, such as integration, automation, targeting, and miniaturization can be utilized to create better biomolecular assays. Specifically, biomolecular assays that can eliminate the need for labeling target biological molecules can reduce the number of process steps and streamline biomolecular assays. Instead of labeling the target biological molecules, or biomolecules for short, the detection can be performed by a surface fixed with a highly specific molecular recognition agent (antibody, aptamer, etc.) to which the target biological molecule binds.

Some biomolecular assays have been developed that are based on such methods of detection that do not involve labeling. One example is surface plasmon resonance (SPR) (e.g. SPR detection using an instrument such as one of commercially available Biacore systems) which can detect as little as 10 fg ($10^{-14}$ g) of a target biomolecule material. Measurements of single binding events of gold-nanoparticle-labeled DNA strands have been reported for an SPR (see reference [1], incorporated herein by reference in its entirety).

Another example of a biomolecular assay that has achieved high sensitivity without labeling is by molecular detection through measurement of resonant frequency shifts that accompany molecular binding within the evanescent field of optical resonators. This is the basis of detection method described herein for a microfabricated optical biomolecular sensor coupled to an optoelectronic swept-frequency semiconductor laser. Microsphere optical resonators shown in references [2, 3], incorporated herein by reference in their entirety, and microring optical resonators shown in references [4, 5], incorporated herein by reference in their entirety, have demonstrated sensor level sensitivity. In fact, single virus binding events have been reported for microring optical resonator sensors (see reference [4]).

SUMMARY

According to a first aspect, an optoelectronic swept-frequency laser system is provided, the system comprising: a semiconductor laser, wherein the semiconductor laser is adapted to emit a coherent optical signal and a frequency of the coherent optical signal is adjustable, in operation, by an injection current input to the semiconductor laser; and an optoelectronic feedback loop, coupled to the semiconductor laser, for providing, in operation, the injection current input based on the frequency of the coherent optical signal, wherein the optoelectronic feedback circuit comprises an optical portion and an electrical portion and wherein the optical portion comprises a signal divider, an interferometer, and a photodetector and the electrical portion comprises a reference oscillator, an electronic mixer, an integrator circuit and a summation circuit.

According to a second aspect, a method for generating a swept-frequency optical signal is provided, the method comprising: generating a coherent optical signal with a semiconductor laser; dividing the coherent optical signal into a fractional feedback optical signal and an emitted optical signal; receiving the feedback optical signal; providing an optical beat signal; converting the optical beat signal to an electronic beat signal; providing an electronic reference signal; combining the electronic reference signal with the electronic beat output signal to form a baseband error signal; integrating the baseband error signal to form an integrated error signal; and combining the integrated error signal with a predistortion signal to form an injection current input for the semiconductor laser, thus generating a swept-frequency optical signal.

According to a third aspect, a method for detecting and measuring biomolecules is provided, the method comprising: providing a swept-frequency optical signal; coupling the swept-frequency optical signal to a resonator, thus producing resonance; delivering a target molecule to the resonator; changing resonance behavior of the resonator by binding the target molecule to a functionalized surface of the resonator; measuring a swept-frequency optical output signal, thus detecting the change in the resonance behavior; and identifying the change in resonance behavior, thus detecting and measuring biomolecules.

Further aspects are shown in the specification, drawings, and claims of the present application.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 2 shows cylindrical, spherical, disk-shaped, and toroidal geometries.

FIG. 4 shows measurement of a whispering gallery mode of a microtoroid optical resonator with quality factor Q=4× $10^7$ using an optoelectronic swept-frequency laser system at 1539 nm.

FIG. 5A shows measurement of wavelength shift of a whispering gallery mode of a microtoroid optical resonator operating at a wavelength of 1539 nm due to absorption of the protein Bovine Serum Albumin (BSA) in a 10 pM solution.

FIG. 5B shows measurement of wavelength shift of a whispering gallery mode of a microtoroid optical resonator operating at a wavelength of 1539 nm due to desorption of the BSA protein from the resonator surface upon exposure of the resonator surface to a 10 mM glycine buffer at pH 1.5.

DETAILED DESCRIPTION

Figure 1:
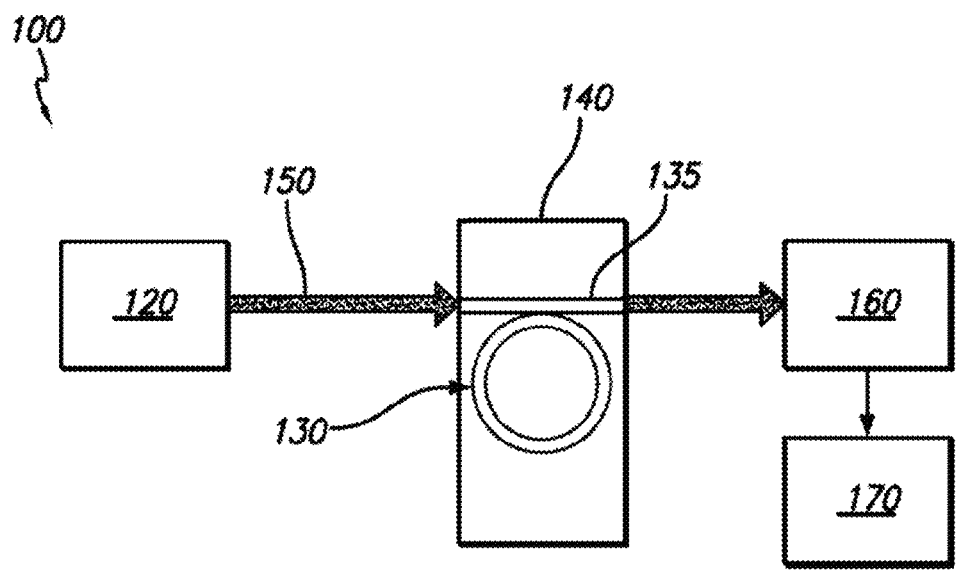
FIG. 1 shows an exemplary biomolecular sensor system with an optical resonator in a microfluidic cell and an optoelectronic swept-frequency semiconductor laser system.

Embodiments of the present disclosure are directed to a biomolecular sensor system comprising an optoelectronic swept-frequency laser (OESFL) and a high-Q microfabricated biomolecular sensor with integrated resonator and waveguide, where the biomolecular sensor system is contained in a microfluidic cell and the resonator surface is functionalized to attract target biomolecules.

Detection of biomolecules has been demonstrated with high-Q optical resonator based sensors, such as a microtoroidal whisper gallery mode resonator, which have been shown to be capable of measurements in solutions as diluted as 100 aM ($10^{-16}$ moles per liter) (as seen in reference [6], incorporated herein by reference in its entirety). Biomolecular detection, especially at the sensitivity level shown in reference [6], could enable detection of low concentration biomarkers not detectable with present analytical methods.

Specifically, high-Q optical resonator based sensors can lead to technologies capable of augmenting or replacing current diagnostic tests such as the prostate specific antibody (PSA) test for prostate cancer. For the specific example of prostate cancer detection, a number of alternate markers for prostate cancer exist that are lower in concentration than PSA but are both more sensitive and more specific to prostate cancer. These markers can be utilized in alternative diagnostic tools for prostate cancer detection if a detector can be built for the markers, as discussed in detail in reference [7], incorporated herein by reference in its entirety. In particular, a biomolecular sensor for prostate cancer can detect the human kallikrein (hK2) marker, which is strongly associated with extracapsular extension and seminal vesicle invasion by prostate cancer, but is present at only 1% of the PSA concentration.

As another example of medical diagnostics utilizing optical resonator based biomolecular sensor is the analysis of vapors and particles in exhaled breath, from laboratory investigations to clinical practice, as a noninvasive diagnostic to determine state of the respiratory tract for such diseases as asthma, cystic fibrosis, and lung cancer. Specifically, biomarkers, such as 8-isoprostane (a marker for inflammation), and a wide range of cytokines have been detected in exhaled breath, but in concentrations so low that large volumes of exhaled breath condensate must be collected over a long period of time to enable detection. Optical resonator based biomolecular sensors, in some embodiments, could be used for such purposes and could reduce sample collection times from currently existing methods, which generally involve collection times of about 10 to 20 minutes. The reduction in sample collection time can also eliminate variable dilution with condensed water vapor associated with long collection time.

High-Q optical resonator based biomolecular sensors typically utilize mechanically-tuned swept-frequency laser. Mechanically-tuned swept-frequency lasers typically comprise mechanical tuning elements that impose some speed, accuracy and reliability limits to the laser frequency sweep. The microtoroidal resonator in many current high-Q optical resonator based biomolecular sensors is fabricated by first utilizing laser heating on a lithographically produced silica disc to melt its perimeter so that it reflows to form a microtoroid accompanied by a dimensional change. In addition, the waveguide in many current high-Q optical resonator based biomolecular sensors is typically made of a tapered optical fiber that is generally positioned mechanically to enable evanescent coupling of the laser source to the optical resonator (i.e., to bring the waveguide to within a few hundred nanometers from the resonator surface).

Applicants disclose herein a biomolecular sensor comprising an optoelectronic swept-frequency laser (OESFL) and a high-Q microfabricated, integrated optical resonator and optical waveguide. The optical resonator and waveguide can be contained in a microfluidic cell.

For clarity purposes, the term "OESFL" is defined herein as an optoelectronic swept-frequency laser system based on a semiconductor laser source combined with an optoelectronic feedback loop, as described in this disclosure. The term "OESFL" may be used interchangeably with "OESFL system" and "OESFL source." The term "optical electronic" is used interchangeably with "optoelectronic" and is defined as a device or method involving both optical and electronic features.

For clarity purposes, the term "swept-frequency", defined herein as adjusting the frequency continuously through a specified range of frequencies at a specified rate of adjustment, is used interchangeably with the terms "sweep frequency", "frequency chirp", "frequency-chirped", "chirp" or "chirped".

For clarity purposes, the term "quality factor" or "Q" is defined herein as a characterization of an optical resonator relating to how long light remains within the cavity of the optical resonator before being lost through mechanisms such as absorption and scattering. A high quality factor implies efficient containment of light, and the term "high-Q" refers to resonators with a quality factor of greater than $10^4$. To exclude single molecule event complication, resonators with quality factors greater than $10^8$ may require separate treatment for specific applications. The present disclosure focuses on resonators with quality factors of $10^4$-$10^7$ to minimize uncertainties associated with Poisson statistics at the single molecule detection limit while still enabling the required sensitivity for a given application. Higher quality factors are possible with special considerations.

For clarity purposes, the term "optical resonator" refers to the optical resonator microfabricated with an integrated waveguide. Even though some embodiments of the present disclosure describe a microtoroidal optical resonator operating in whispering gallery mode, the biomolecular sensor of the present disclosure can comprise an optical resonator operating in whispering gallery mode or other modes such as guided mode. In addition, the optical resonator can be of geometries other than microtoroid, for example it can be of ring-shaped, disk-shaped, spherical or cylindrical geometries.

For clarity purposes, the term "biomolecule" can be used interchangeably with "biological molecule" and is defined as any biologically relevant molecule such as proteins, carbohydrates, antibodies, DNA, lipids, fatty acids and derivatives thereof. Biomolecules may be naturally occurring or synthetically derived analogs of naturally occurring molecules.

Referring now to FIG. 1, shown herein is a biomolecular sensor (100) comprising an optoelectronic swept-frequency laser (OESFL) system (120), a high-Q microfabricated, optical resonator (130), and an integrated waveguide (135). The optical resonator (130) and integrated waveguide (135) are contained in a microfluidic flow system (140). The optical resonator (130) has a surface which is functionalized to bind to specific target biomolecules, such that the binding of the biomolecules lead to a measurable change in resonance behavior. The OESFL system (120) is coupled to the integrated optical resonator and waveguide (130) by one or more external waveguides (150) to a sensor photodetector (160) which converts an optical signal to a current signal that is sent to a signal processing unit (170).

The sensor photodetector (160) can be any detector that measures the intensity of the light exiting the external waveguide (150). The detected photocurrent is sampled and digitized and fed into the signal processing unit (170). This can comprise either a computer, or any processing unit capable of determining the amount of shift of the resonant frequency, typically calculated by fitting a theoretical line shape to the measured data. All analysis can be done during data collection (i.e. live) or post data collection. One embodiment of the signal processing unit comprises an oscilloscope to read in the signal and a computer that measures and plots the resonance shift in real time.

1. Optical Resonator Design

Optical cavity sensor devices can be characterized by their quality factor, Q, which is related to how long light remains within the cavity before being lost through mechanisms such as absorption and scattering. A high quality factor implies efficient containment of light, with some resonator geometries exhibiting a Q value as high as $10^{10}$ (as shown in reference [12], incorporated herein by reference in its entirety).

An optical cavity detection assay can be used to sense changes in the environment surrounding (e.g., ambient temperature, pressure, surrounding fluid content, and so forth) a high-Q optical resonator. In a whispering-gallery-mode resonator, light circulates around the periphery of the resonator, undergoing total internal reflection at the silica-fluid interface and making as many as $10^5$ revolutions. An evanescent field penetrates into the fluid surrounding the silica resonator as an evanescent wave. Biomolecules that bind to the sensor surface change the effective refractive index of the mode. The change in effective refractive index results in a shift in resonant frequency of the cavity.

A previous study (shown in reference [11], incorporated herein by reference in its entirety) was able to show single-molecule binding events of Interleukin-2 to a surface-bound monoclonal antibody immobilized on the sensor in both water and in bovine serum.

The detection assay itself is performed by monitoring the shift in the resonant frequency within the optical cavity of the resonator. As shown in FIG. 1, light from an optoelectronic swept-frequency laser (OESFL) system (120) is coupled into the optical resonator (130) through the integrated waveguide (135), and the resonant frequency is determined by monitoring the transmission through the integrated waveguide (135) and one or more external waveguides (150) during a scan through frequency-space. FIG. 4 shows measurement of a whispering gallery mode of a microtoroid optical resonator with quality factor $Q=4\times10^7$ using an optoelectronic swept-frequency laser source at 1539 nm. The resonant frequency is identified as a minimum in the transmission spectrum, and accuracy of this measurement improves with higher quality factor (lower resonance linewidth).

Figure 2:
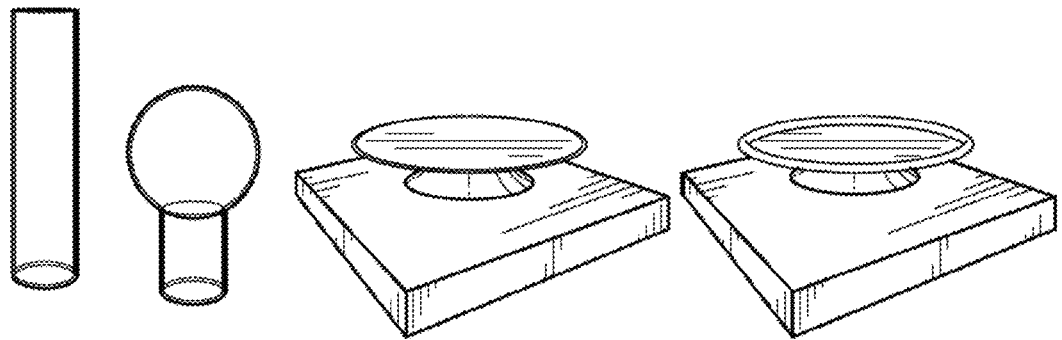
FIG. 2 shows exemplary whispering gallery mode resonator geometries. Specifically.

A variety of high-Q resonator geometries have been demonstrated, including cylindrical, spherical, disk-shaped, and toroidal, as shown in FIG. 2. Some other possible resonator geometries include oblate spheroid, ring-shaped and others.

These resonators are typically on the micro-scale when used for sensing applications, with diameters in the range of 50-150 µm. This size range reduces radiation losses associated with small diameters and increases analyte (also known as target biomolecule) transport rates to the sensor while ensuring sparse modes in wavelength space that are easy to find.

Microdisks, microrings, and microtoroids can be implemented through standard CMOS microfabrication techniques, while implementations of microspheres, microcylinders and microtoroids generally involve a fabrication step to decrease surface roughness of the resonator. This step of decreasing surface roughness reduces surface scattering, thus increasing the quality factor, and is accomplished either by polishing or melting. However, change in the size of resonator that occurs during this process generally involves precise positioning of optical components to couple light into the resonant mode of the optical element.

With reference back to FIG. 1, Applicants disclose herein a method to microfabricate the high-Q optical resonator (130), integrated waveguide (135) and portions of the microfluidic cell (140) using well-established CMOS semiconductor planar microfabrication techniques such as e-beam microlithographic patterning followed by a first reactive ion etch to define a first set of features such as the optical resonator (130), the integrated waveguide (135), and the walls and floor of the microfluidic cell (140) from a selected substrate material suitable for the application. The selected substrate material can be a bilayer material such as silicon-on-insulator or silicon nitride on silica. A deposition of a second material can be performed after the first reactive ion etch, followed by a second microlithographic patterning and a second etch to generate a second set of features in the second material. For example, silica can be deposited, patterned by optical microlithography and etched by reactive ion etch to form spot size converter for the integrated waveguide (135) as well as liner layer for the walls and floor of the microfluidic cell (140).

The resonator (130) with integrated waveguide (135) can then be coupled to the OESFL (120) and the sensor photodetector (160) utilizing one or more external waveguides (150). The sensor photodetector (160) is further coupled to a sensor processing unit (170), thus fabricating the biomolecular sensor shown in FIG. 1.

Figure 10:
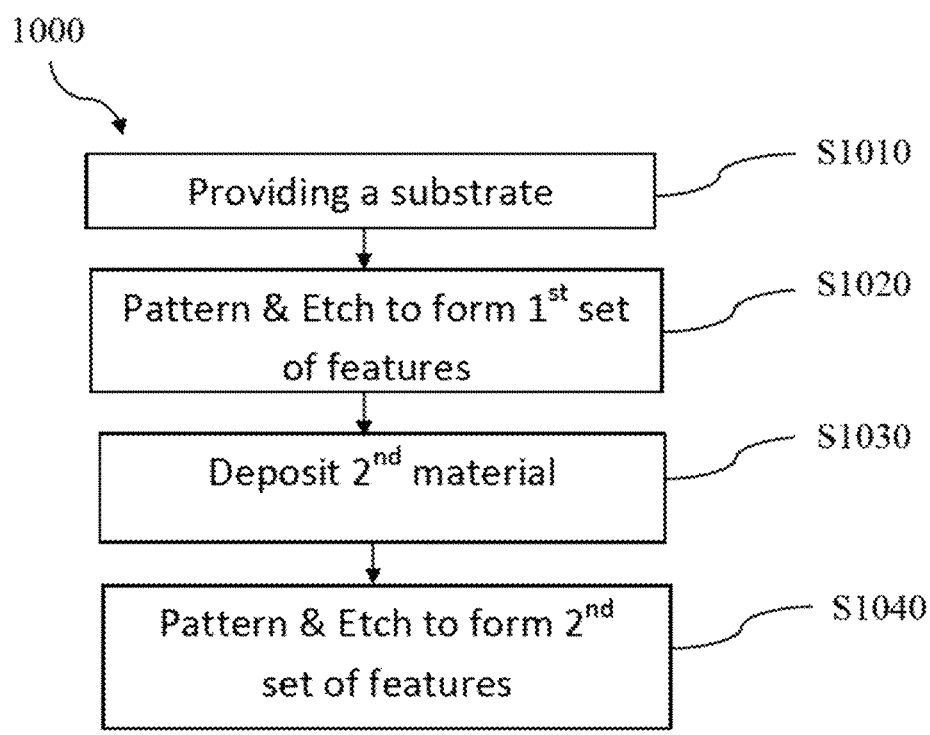
FIG. 10 shows a flow chart of a method of fabrication for an optical resonator with integrated waveguide in a microfluidic cell, for a biomolecular sensor, in a further embodiment of the present disclosure.

FIG. 10 shows a flow chart of a method (1000) of fabrication of an optical resonator with integrated waveguide in a microfluidic cell, for a biomolecular sensor, in a further embodiment of the present disclosure. The method (1000) includes: providing a substrate (S1010), pattern and etch the substrate to form first set of features (S1020), and deposit a second material (S1030), pattern and etch second material to form a second set of features (1040).

Specifically, the choice of substrate material(s) for the resonator (130) and waveguide (135) can depend on wavelength of operation, e.g. substrate material(s) can be chosen to minimize absorption and scattering losses. Resonators (130) and waveguides (135) fabricated on a silicon-on-insulator substrate to form silicon resonators (130) and silicon waveguides (135) on the insulator, which is typically oxide. Silicon resonators (130) and silicon waveguides (135) can be used for operation in the infrared regime (>1.1 microns). Silicon nitride resonators (130) and waveguides (135) can be microfabricated on a silicon nitride on silica substrate and can be used for operation in the visible and near-infrared regions. From the selected substrate material, shape of the resonator (130) and distance between the resonator (130) and the waveguide (135) can be defined by optical or e-beam type of microlithography.

Figure 9A:
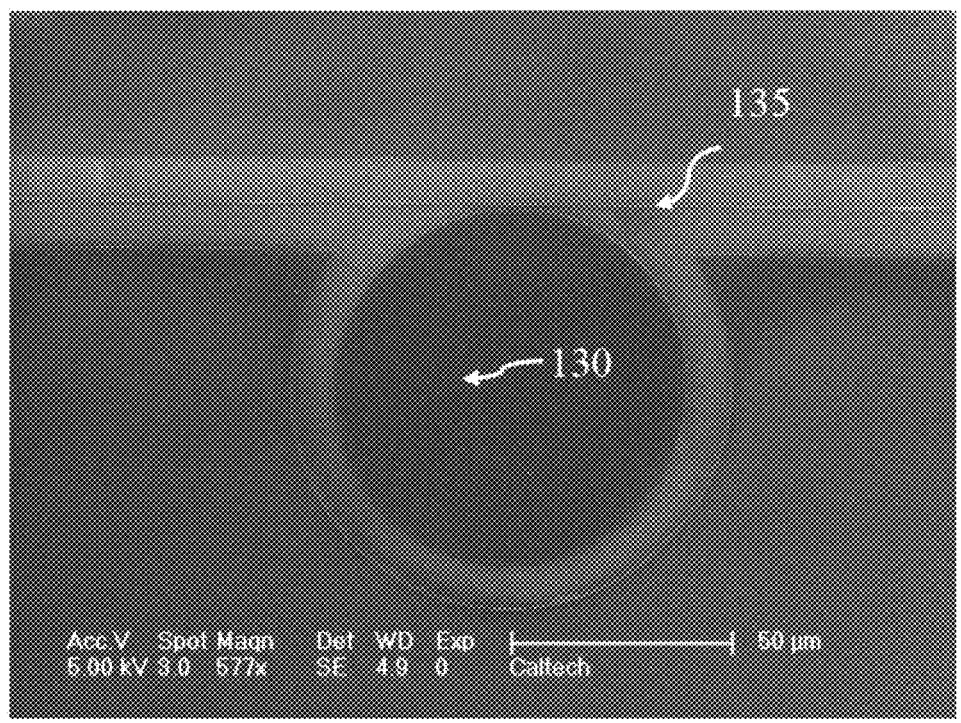
FIGS. 9A and 9B show an electron micrograph and a close-up electron micrograph of an exemplary high-Q microfabricated optical resonator with a planar, microfabricated, integrated waveguide for coupling light into the optical resonator.
Figure 9B:
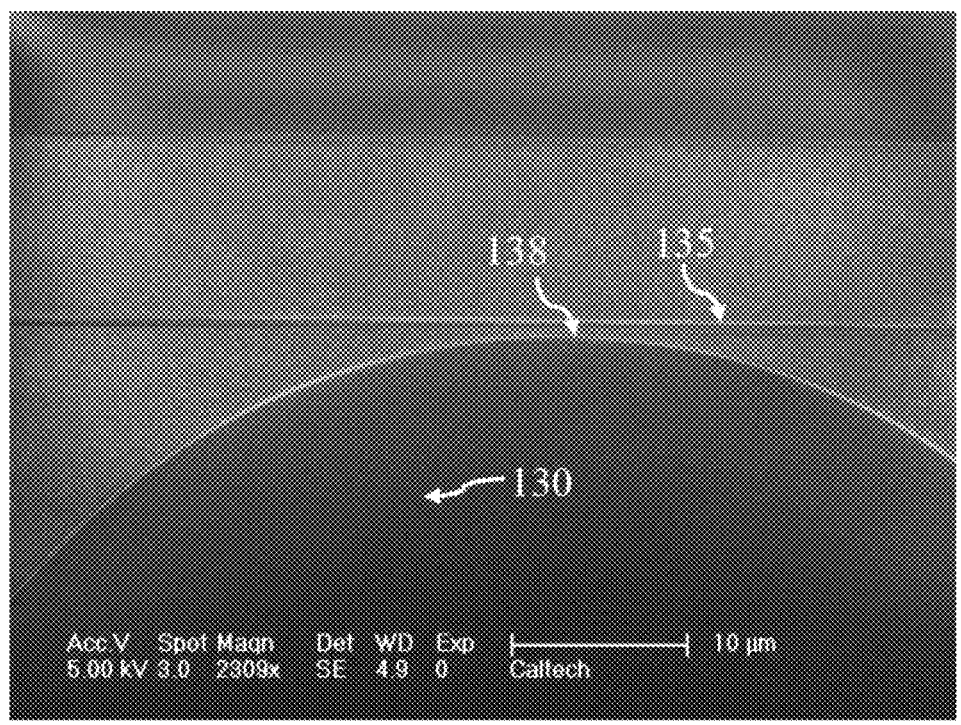

FIGS. 9A and 9B show an electron micrograph and a close-up electron micrograph of an exemplary high-Q microfabricated microdisk optical resonator (130) with a planar, microfabricated, integrated waveguide (135) for coupling light into the optical resonator (130). Light from the waveguide (135) can be evanescently coupled, for example, into a high-Q whisper gallery mode of the microdisk optical resonator (130). The spacing (138), shown in FIG. 9B, between the waveguide (135) and the cavity of the optical resonator (130) can be optimized to achieve near-critical coupling for efficient energy transfer between the waveguide mode and the whisper gallery mode as shown in reference [13], incorporated by reference in its entirety. Lithographically controlling the waveguide-resonator coupling can eliminate the need for precise manual alignment of a waveguide, typically a tapered optical fiber, within tens of nanometers of the resonator surface, and can make the biomolecular sensor (100) of FIG. 1 more robust for applications such as point-of-care diagnostics.

Figure 11A:
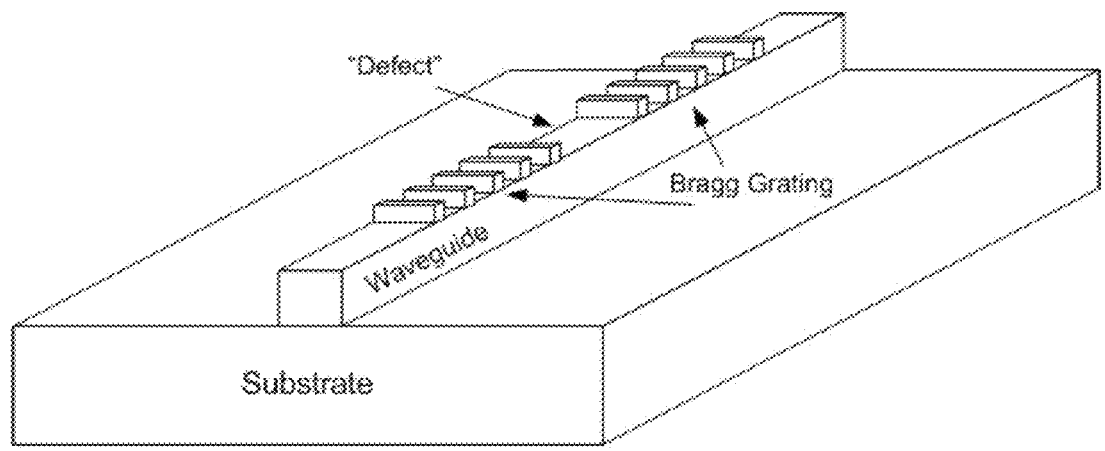
FIG. 11A shows a drawing of an exemplary Bragg resonator.
Figure 11B:
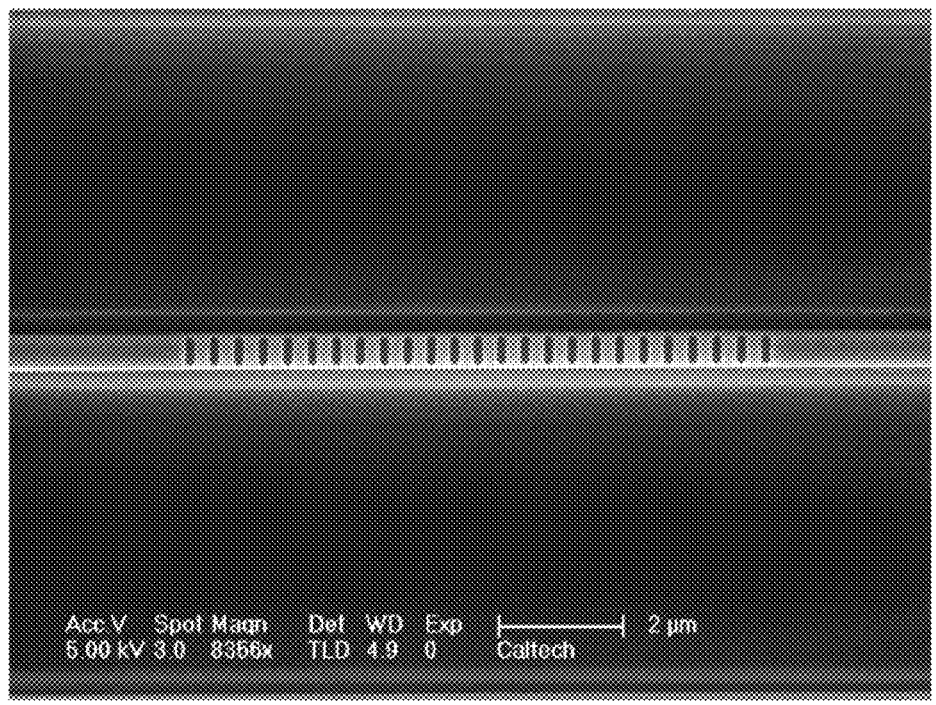
FIG. 11B shows an electron micrograph of an exemplary microfabricated Bragg resonator.

Other optical resonator geometries can exhibit high quality ($Q>10^4$) and be microfabricated with integrated waveguide by the methods state above. A possible resonator geometry is a Bragg resonator, which is an optical cavity formed using Bragg reflectors as the confining mirrors. In general, the Bragg resonator can be one-dimensional or two-dimensional (e.g. a photonic crystal cavity). It should be noted that a system using a Bragg resonator is not operating in a whispering gallery mode. Light bounces back and forth between the Bragg reflectors rather than circulating at the circumference as in a whispering gallery mode. Further, the field is not coupled evanescently from the waveguide to the resonator as with the other resonators discussed in the present disclosure. The (1-D) Bragg resonator is an "inline" resonator where the resonator is incorporated as a part of the waveguide. This design can eliminate or reduce need for precise coupling and alignment from the OESFL system. FIG. 11A shows a drawing of an exemplary Bragg resonator, and FIG. 11B shows an electron micrograph of an exemplary microfabricated Bragg resonator.

2. Optoelectronic Swept-Frequency Laser

Figure 3:
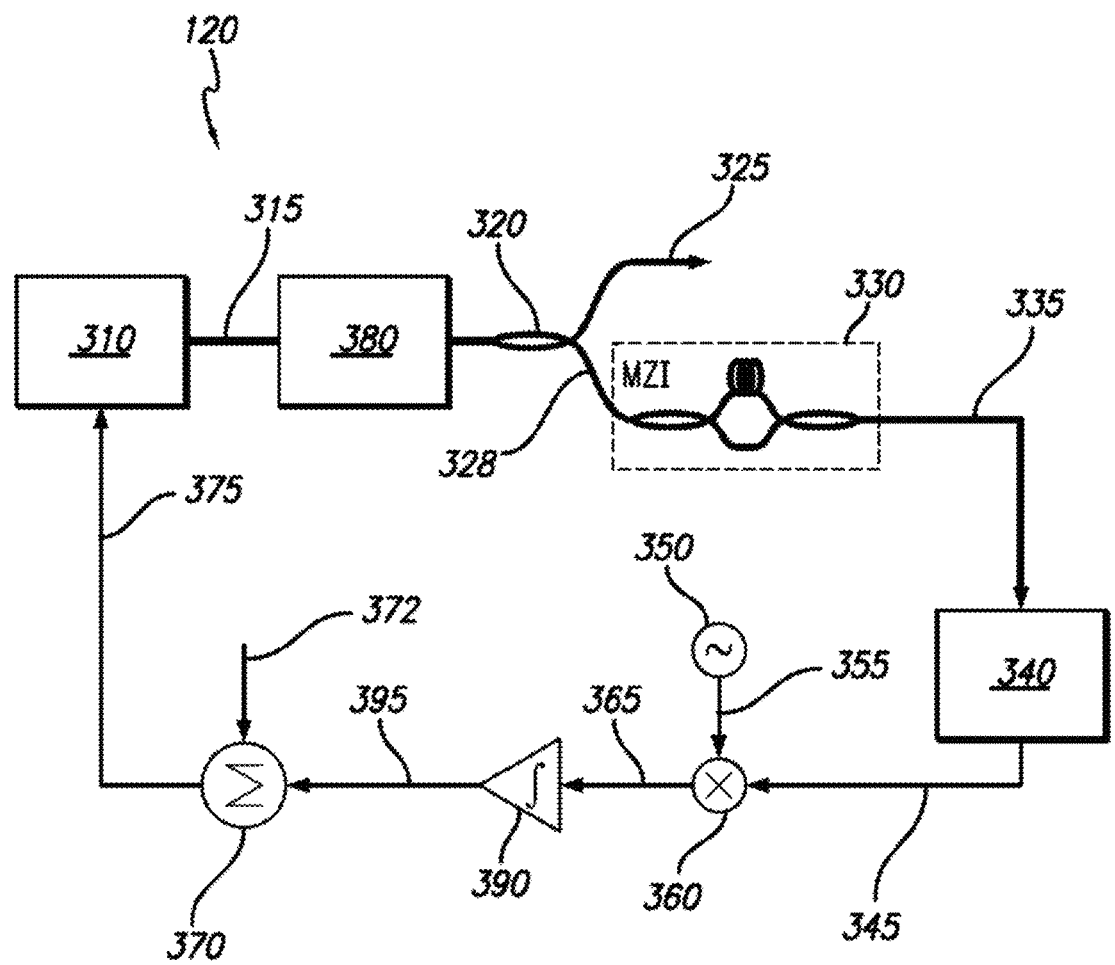
FIG. 3 shows an exemplary schematic of an optoelectronic feedback loop of an optoelectronic swept-frequency laser system.

The biomolecular detector (100) of FIG. 1 comprises an optoelectronic swept-frequency laser (OESFL) system (120) in addition to the optical resonator (130) and other parts. FIG. 3 shows the optoelectronic swept-frequency laser system (120) comprising a semiconductor laser (SCL) (310) and an optoelectronic feedback loop for the SCL (310).

The semiconductor laser (310) is designed to emit a coherent optical signal (315). A frequency of the coherent optical signal (315) can be adjusted by an injection current input (375) to the semiconductor laser (310), provided by the optoelectronic feedback loop based on the coherent optical signal (315).

The optoelectronic feedback loop, also referred to as optoelectronic feedback circuit, comprises an optical portion and an electrical portion. The optical portion comprises a signal divider (320), an interferometer (330), and a photodetector (PD) (340) and the electrical portion comprises a reference oscillator (350), an electronic mixer (360), an integrator circuit (390) and a summation circuit (370). The loop can be reset periodically, with period T. An amplitude control loop (380) can be utilized to ensure that the optical output has uniform amplitude.

The coherent optical signal (315) output from the SCL (310) can go through the optoelectronic feedback loop starting with a 90/10 coupler, which is also referred to as a signal divider (320). By dividing the coherent optical signal (315) output from the SCL (310), a small portion (10%) of the coherent optical signal (315) output from the SCL (310) is coupled into the optoelectronic feedback loop as a feedback optical signal (328). The remaining 90% of the coherent optical signal (315) is an emitted optical signal (325) of the OESFL (120).

The feedback optical signal (328) continues through an interferometer (330), such as a fiber Mach-Zehnder Interferometer, where the feedback optical signal (328) is received and divided into a first portion with differential time delay ti and a second portion without differential time delay. The two portions of the feedback optical signal (328) are combined by the interferometer (330) to provide an optical beat signal (335)

The optical beat signal (335) from the interferometer (330) is incident on a photodetector (340). The photodetector (340) converts the optical beat signal (335) from the interferometer (330) interferometer into an electronic beat signal (345).

The electronic beat signal (345) is mixed down by an electronic mixer (360) with a high coherence electronic reference signal (355) at frequency $\omega_R$ provided by a reference oscillator (350) to form a baseband error signal (365).

The baseband error signal (365) is integrated with an integrator circuit (390) to form an integrated error signal (395) which is combined by a summation circuit (370) with a predistortion signal (372) to produce a current ramp as the injection current input (375). The injection current input (375) is fed back into the SCL (310) to generate a nominally linear chirp, or frequency sweep, in the coherent optical signal (315) output from the SCL (310).

The open loop predistortion signal (372) can enhance the linearity of the coherent optical signal (315) and the emitted optical signal (325). The predistortion signal (372) is a monotonically varying current that is designed to produce a nominally linear frequency vs. time output at the SCL (310). The shape of the predistortion signal (372), which is a current signal, is determined by measuring the optical output frequency vs. time profile ("shape of the frequency chirp") when a linear current ramp is applied to the injection current input (375) and using the measured data to back-calculate the shape of the predistortion signal (372) involved in producing a linear frequency chirp. This process is repeated iteratively to achieve higher accuracy.

Rather than stating a formal and lengthy analysis used for the design and simulation of the OESFL system (120), Applicants show that a linear chirp or sweep in frequency is the steady-state solution of the arrangement shown in FIG. 3. A linear optical frequency sweep input to the interferometer, shown in FIG. 3 as the feedback optical signal (328), results in a sinusoidal intensity modulation at its output, shown in FIG. 3 as the optical beat signal (335). The optical beat signal (335) is converted into a sinusoidal current at the output of the photodetector (340), shown as the electronic beat signal (345) of FIG. 3.

This electronic beat signal (345) beats with the input electronic reference signal (355) to yield a zero frequency output, shown as the integrated error signal (395) that is then integrated and combined with the predistortion signal (372) to produce a linear ramp injection current input (375) to the SCL (310). This results in a linear frequency sweep in the coherent optical signal (315) of the SCL (310).

A linear frequency vs. current response of the SCL (310) is not a requisite. Deviations from linearity will lead to an output (345) from the photodetector (340) that is not a pure sinusoid, and thus lead to a correction of the injection current input (375) applied to the SCL (310), which will persist until linearity is achieved.

Formally, when the loop is in lock, the frequency of the SCL is given by $$\omega_{SCL} = \omega_0 + \xi t \quad (1)$$

where $\xi$ is the slope of the optical frequency sweep. The corresponding optical phase is given by $$\phi(t) = \phi_0 + \omega_0 t + \frac{1}{2}\xi t^2. \quad (2)$$

The photocurrent of the photodetector is therefore given by $$i_{PD}(t) = K_P \cos(\phi(t) - \phi(t-\tau)) = K_P \cos\left(\xi\tau t + \omega_0\tau - \frac{\xi\tau^2}{2}\right), \quad (3)$$

where the photodetector gain Kp is given by the product of incident optical power and photodetector responsivity. The DC term in Eq. (3) has been ignored. The result is a sinusoidally varying photodetector current whose angular frequency $\omega_{PD}$ is given by the slope of an initial frequency chirp $\xi$ and a time delay of the interferometer $\tau$, i.e. $\omega_{PD} = \xi\tau$. The detected photocurrent is mixed with an electronic reference signal with phase ($\omega_R t + \phi_R$), and the difference frequency output of the mixer is given by $$i_M = K_P K_M \cos\left(\xi\tau t - \omega_R t + \omega_0\tau - \frac{\xi\tau^2}{2} - \phi_R\right), \quad (4)$$

where $K_M$ is the mixer gain. In steady-state, the mixer current $i_M$ is a constant DC signal; this implies that the phase of Eq. (4) is a constant $\phi_{DC}$. Therefore, $$\xi = \frac{\omega_R}{\tau} \quad (5)$$

and $$\omega_0 = \frac{\phi_R + \phi_{DC} + 2m\pi}{\tau}, \quad (6)$$

where m is an integer, and Applicants have used $\xi\tau^2 \ll 1$. This DC signal, when integrated and fed back into the laser, generates the linear optical frequency chirp in Eq. (1).

The above analysis shows the loop to be self-consistent in steady state. The linearity of the frequency chirp is characterized by the output photocurrent given by Eq. (3). When in steady state, the slope of the optical frequency chirp is locked to the frequency of the reference oscillator, and the starting frequency is determined by the phase of the reference oscillator, as shown in Eqs. (5) and (6). Stability of the starting frequency is important in sensing applications, where repeatability of frequency sweeps is essential. A small signal analysis around the steady state point given by Eqs. (5) and (6) shows that phase noise of the laser within the loop bandwidth is corrected by the feedback loop as shown in reference [8], incorporated herein by reference in its entirety. This can reduce the laser instantaneous linewidth and thus enhance coherence length of the laser source. The optoelectronic swept-frequency laser described above generally has no moving parts, and can be a compact, inexpensive and reliable laser source for many applications.

Figure 7:
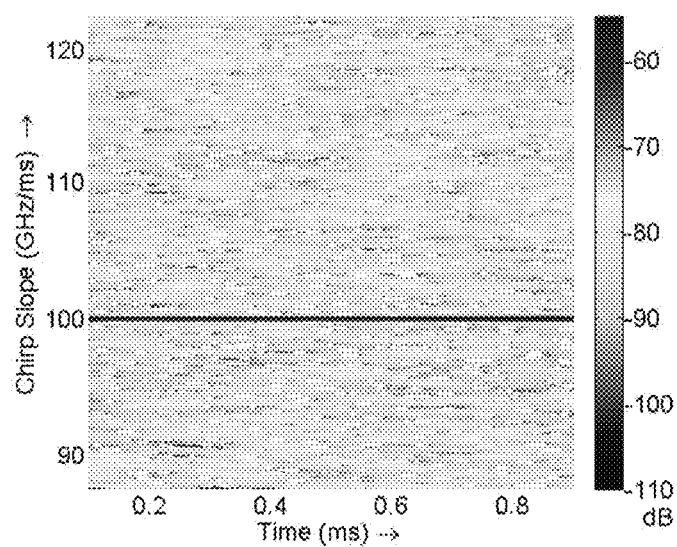
FIG. 7 shows a plot of slope of optical chirp vs. time, where linear optical chirp is generated by an exemplary optoelectronic swept-frequency laser system.
Figure 8:
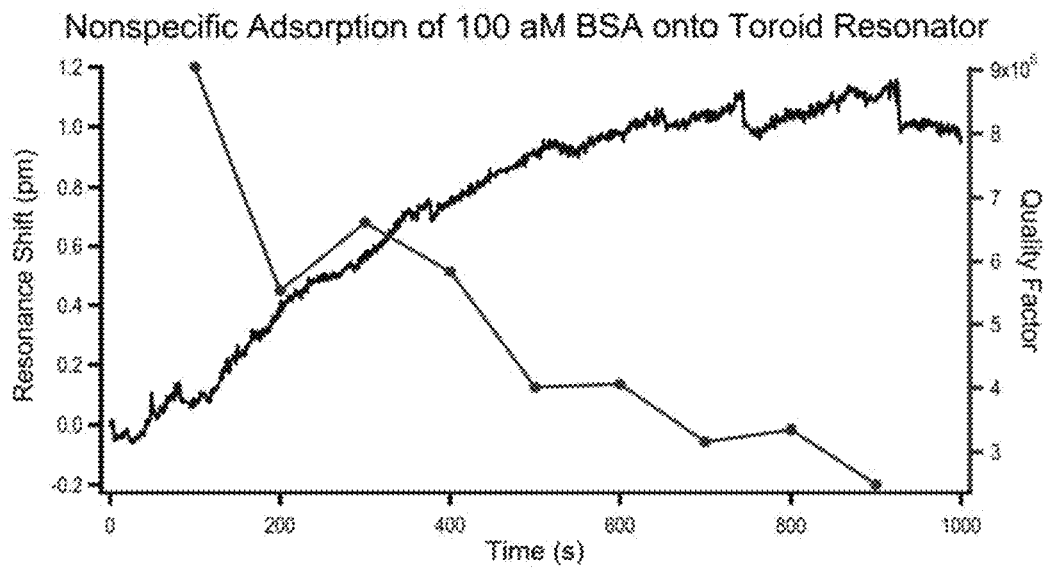
FIG. 8 shows resonant wavelength shift (continuous) and change in Q (points with connections) over time for nonspecific adsorption of 100 aM BSA onto an exemplary bare silica microtoroid optical resonator.

Applicants have demonstrated highly linear frequency chirps using a distributed feedback laser at a wavelength of 1550 nm in an optoelectronic feedback loop as shown in reference [8]. The slope of the frequency chirp and its starting frequency are locked to the frequency and phase, respectively, of a high coherence electronic oscillator. FIG. 7 shows a plot of the slope of the laser chirp as a function of time. The slope is constant at 100 GHz/ms, indicating that the chirp has a degree of linearity. Both tuning range and rate of optical chirps can be further improved for these systems. Range resolution experiments, conducted by imaging front and back surfaces of acrylic sheet have verified that resolutions of <0.2 mm are achieved.

3. Wavelength of Operation, Linewidth and Sweep Range

Operating wavelength of the OESFL can be chosen based on an intended application. Choosing an appropriate wavelength that minimizes absorption losses in water can be valuable for biological sensing applications. Another metric for considering suitability of an OESFL for sensing applications are range of the frequency chirp and instantaneous linewidth of the laser.

Table 1 shows absorption coefficient of water from reference [14], incorporated herein by reference in its entirety, at different wavelengths of interest. It is clear that low absorption in the visible range of the spectrum makes this wavelength regime better for sensing, since sensitivity of devices such as optical resonators and SPR sensors is enhanced due to the reduction of water absorption losses and consequent improvement of the quality factor at the resonant frequencies.

TABLE 1

| Wavelength (nm) | Extinction Coefficient | Absorption Coefficient ($m^{-1}$) |
|---|---|---|
| 625 | $1.39 \times 10^{-8}$ | $2.80 \times 10^{-13}$ |
| 675 | $2.23 \times 10^{-8}$ | $4.15 \times 10^{-13}$ |
| 1060 | $1.0 \times 10^{-6}$ | $1.2 \times 10^{-11}$ |
| 1300 | $1.1 \times 10^{-5}$ | $1.1 \times 10^{-10}$ |
| 1550 | $1.6 \times 10^{-4}$ | $1.3 \times 10^{-9}$ |

Total chirp range of the laser source for use in sensing may not a critical factor, since the typical wavelength shifts range caused by the binding of biochemical molecules is less than 0.1-1 nm, as shown in reference [15], incorporated herein by reference in its entirety. Tuning ranges of approximately 1 nm, which is typical for distributed feedback SCLs, are therefore sufficient to track resonances as they shift in frequency due to protein binding events. The wavelength tuning range can be further extended by using arrays of tunable lasers or by the process of four wave mixing as to access larger regions of the optical spectrum.

Further, high-sensitivity sensing measurements rely on the measurement of high-Q resonators whose resonances have quality factors on the order of around $10^7$ and $10^8$ as shown in [18], incorporated herein by reference in its entirety. In order for an OESFL to resolve a particular resonance, its instantaneous linewidth needs to be an order of magnitude narrower than the linewidth of the resonance to be investigated. From Table 2, at a center wavelength of 1550 nm, a linewidth on the order of 1 MHz involved in discerning a resonance with Q of around $10^7$. At 1 μm the linewidth involved in discerning a resonance is nearly 3 MHz, whereas at 625 nm a 5 MHz linewidth would suffice. These linewidths can be met by commercially available SCLs. Table 2 shows values of exemplary maximum allowable linewidths for optoelectronic swept-frequency laser devices in exemplary biomolecular sensors with quality factors (Q) of $10^7$ and $10^8$.

TABLE 2

| Wavelength (nm) | Frequency (Hz) | Linewidth (MHz) Q = $10^7$ | Linewidth (MHz) Q = $10^8$ |
|---|---|---|---|
| 625 | $4.8 \times 10^{14}$ | 48 | 4.8 |
| 675 | $4.4 \times 10^{14}$ | 44 | 4.4 |
| 1060 | $2.83 \times 10^{14}$ | 28 | 2.8 |
| 1300 | $2.3 \times 10^{14}$ | 23 | 2.3 |
| 1550 | $1.94 \times 10^{14}$ | 19 | 1.9 |

Experiments by the Applicants using an optoelectronic OESFL developed for telecommunication wavelengths (shown in reference [8]) and a high-Q microtoroid resonator have demonstrated ability of the laser to resolve high-Q resonances for sensing applications. FIG. 4 shows measurement of a resonant whispering gallery mode of a silica microtoroidal resonator in air at a wavelength of 1539 nm. The resonance exhibits a characteristic splitting owing to a break in the degeneracy of the two counter-propagating modes of the resonator due to scattering of light. The mode with a quality factor $4 \times 10^7$ is clearly resolved by the measurement, demonstrating the narrow instantaneous linewidth of the laser source.

Sensing experiments involve precise control over starting frequency and frequency chirp slope. FIGS. 5A and 5B show effective of the laser source as an investigation tool for liquid-phase sensing applications. FIG. 5A shows shift in resonant wavelength of a whispering gallery mode of a microtoroid resonator sensor as a 10 pM solution of the protein Bovine Serum Albumin (BSA) flows across the resonator in the microfluidic cell. FIG. 5B shows the wavelength shift due to desorption of the BSA protein from the sensor surface during flow of 10 mM glycine buffer at pH 1.5. The wavelength shift is easily resolved by the OESFL, and it is expected that protein concentrations that are smaller by 1-2 orders of magnitude can be resolved at this wavelength. Applicants note that this measurement involves non-specific binding of BSA to a silica resonator, whereas specific sensing is possible with functionalized surface discussed in section 5.

The limiting factor of Q values, or quality factor, in the experimental results shown in FIGS. 5A and 5B seems to be the wavelength of operation. The quality factor of the resonant mode in air is $4 \times 10^7$, but the quality factor becomes around $2 \times 10^4$ in aqueous solution due to the absorption loss in water. This decrease in quality factor can be attributed to the increase in the linewidth of the resonance and can limit the minimum measurable wavelength shift, and hence the sensitivity of the measurement. The utilization of OESFL systems at lower wavelengths such as 600-700 nm and 1 μm can enhance the measurement sensitivities, potentially to the single molecule detection limit.

4. Waveguides and Optical Coupling

The OESFL system (120) of FIG. 1 can be coupled with the resonator (130) and integrated waveguide (135) by one of two methods. In a first method, the OESFL system (120) and the optical resonator (130) as well as the integrated waveguide (135) and the external waveguides (150) can be microfabricated on the same chip or platform, e.g. on the same wafer.

In a second method, the optical mode from the output of the OESFL system (120) can be coupled to the smaller optical mode of integrated waveguide (135) by using an optical fiber, such as using a spot-size converter (see references [25, 26], incorporated herein by reference in their entirety) based on adiabatic mode transformation (see reference [27], incorporated herein by reference in its entirety), where the optical mode is transformed from the larger fiber mode to the smaller waveguide mode with very low loss.

5. Sensor Functionalization

Surface of the optical resonator can be functionalized to bind to a specific biomolecule of interest. Most covalent surface functionalization schemes as shown in reference [19], incorporated herein by reference in its entirety, either degrade sensitivity of the sensor by introducing scattering or absorptive losses or reduce efficacy of the surface functionalization for binding to a target biomolecule.

Applicants have developed a method for functionalizing resonators for specific sensing that avoids this quality factor degradation. A bi-functional linker molecule with a polyethylene glycol (PEG) backbone proven to resist non-specific protein adsorption as shown in references [20, 21], incorporated herein by reference in their entirety, is attached to a triethoxysilane monolayer on the resonator that presents an azide group. The first functional group on the linker molecule is an alkyne which reacts with the azide group through copper (I)-catalyzed cycloaddition in references [22, 23], incorporated herein by reference in their entirety. This so-called "click chemistry" reaction takes place under mild and biologically inert conditions. The second functional group on the linker molecule is a maleimide for reaction with available cysteine residues or thiol groups on the targeting molecule necessary for specific sensing.

Figure 6A:
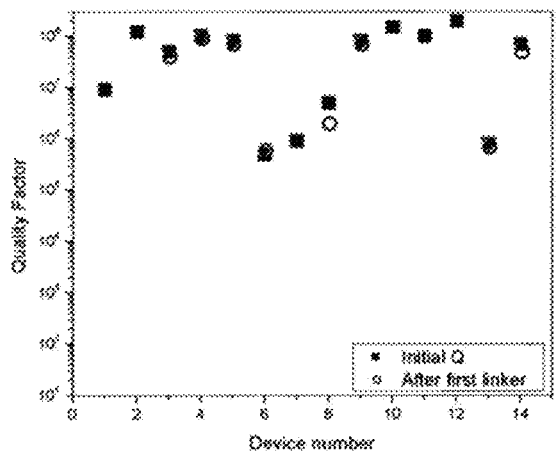
FIG. 6A shows quality factor decrease for a whispering gallery mode of a microtoroid optical resonator operating at a wavelength of 1539 nm following a first linker attachment of click-chemistry labeling of the resonator surface.
Figure 6B:
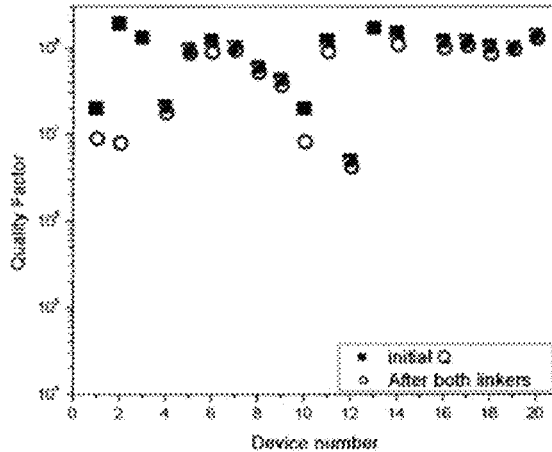
FIG. 6B shows quality factor decrease for a whispering gallery mode of a microtoroid optical resonator operating at a wavelength of 1539 nm following a second linker attachment of the click-chemistry labeling of the resonator surface.

Through these methods, Applicants have an adaptable platform with possible environmental stability and specificity without sacrificing sensor performance. FIGS. 6A and 6B show the quality factor change measured for a number of resonators after labeling with the bi-functional linker molecule that has not been attached to a targeting molecule. Applicants note that in most cases, the reduction of Q was much less than a factor of 2. Antibodies are particularly interesting targeting agents at least because of their high specificity, commercial availability, and tendency to present cysteine residues that are useful in the functionalization reactions.

Oligonucleotide apatamers as shown in reference [24], incorporated herein by reference in its entirety, represent another option as a molecular recognition tool. These are short DNA or RNA strands which have been developed with sequences that bind specifically a variety of protein and small-molecule targets while demonstrating remarkable selectivity against structural analogs. Because such oligonucleotides can be easily synthesized with thiol groups at one end, they are attractive candidates for incorporation into the same click chemistry-based sensor functionalization platform as antibodies.

6. Microfluuidic Flow System

The biomolecular sensor may involve a microfluidic flow system, or microfluidic cell, to efficiently deliver a target analyte to the sensor. The microfluidic flow system can allow for a liquid sample to flow and surround the optical resonator within a sealed and sterile environment. Two methods are disclosed herein for the incorporation of the microfluidic flow system. In a first method, the microfluidic flow system can be added to the chip containing the microfabricated optical resonator and integrated waveguide.

A second method is to fabricate the microfluidic system in conjunction with the resonator and integrated waveguide. Specifically, the walls for the microfluidic flow system or microfluidic cell can be formed in the substrate at the same time as the resonator and integrated waveguide utilizing microfabrication methods such as microlithography and etching. The microfluidic flow system can be subsequently sealed by the addition of a polymer or glass ceiling to the microfluidic cell. The sealing would create an enclosed microfluidic cell containing the resonator and the integrated waveguide.

The microfluidic flow system can have micro-scale flow channels which allow a user to deliver small volumes of sample to the biomolecular sensor. This flow system would also include inlet and outlet ports.

7. Examples

Design and Demonstration of Precisely Controlled Optoelectronic Chirped Laser Source Embodiments of the present disclosure include development and design an OESFL system at wavelengths suitable to liquid phase sensing. The specific method steps include design and experimental demonstration of linear frequency chirp SCLs at 600-700 nm and/or 1 µm with linear frequency chirp with a tuning range >1 nm and with a frequency tuning rate >$10^{14}$ Hz/s. Measurement and characterization of the chirped OESFL system can include 1) tuning range of the swept-frequency OESFL, 2) tuning speed of the swept-frequency-OESFL, and 3) theoretical analysis of the effect of tuning range and speed on laser linewidth.

The performance of the optoelectronic source can be characterized and improved. The limitations of the optoelectronic feedback loop of the OESFL system on the chirp rate can be studied theoretically and experimentally. The effect of tuning speed on the instantaneous laser linewidth, which determines the resolution of a sensing measurement, can be experimentally investigated. An amplitude control loop to compensate for the variation in the laser output power due to current tuning can be designed and demonstrated.

Development of Optical Resonator for Biomolecular Sensing

Resonator geometries such as the Bragg resonator and the microring resonator can be developed. Materials such as $Si_3N_4$ can be investigated for the microfabricated optical resonator with integrated waveguide of the present disclosure.

8. Other Applications

The linearly chirped OESFL system can have other applications, such as high-resolution 3-D optical imaging. A part of the laser output illuminates the imaging target, or object to be imaged, and the reflected light accumulates a time delay depending on the location of the imaging target. When the reflected light is mixed with an un-delayed laser output in a photodetector, the resultant photocurrent varies sinusoidally with a frequency proportional to the time delay. The number of reflections and their distances are determined by measuring the frequencies present in the detected photocurrent. The beam or the imaging target is then scanned in the lateral direction to obtain a three dimensional image.

The OESFL can replace current state-of-the-art mechanically tuned lasers as the source of a linearly chirped optical waveform. The elimination of moving parts, and rapid and precise tuning of the optical frequency via an electronic current can improve cost, size, and robustness. Further, the OESFL can have a lower phase noise than typical mechanically tuned lasers, which can translate to better imaging depth in imaging techniques such as swept source optical coherence tomography. The OESFL may be more limited in its tuning range, but the tuning range of OESFL can be increased by methods such as four-wave mixing or electronic stitching.

The development of OESFLs at lower wavelengths 0.6-1.1 microns and 1.3 microns as disclosed in the present disclosure can enable imaging of targets in media where absorption by water can be a major concern. Propagation loss for light is lower at lower wavelengths. Examples of possible applications include 3-D imaging of biological tissue such as the imaging of the retina through the vitreous humor in the eye.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. For example, the person skilled in the art will understand that the number of steps or components shown is only indicative and that the method can occur in more or fewer steps and that the system may contain more or less components according to the various embodiments. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

REFERENCES

[1] T. Sannomiya, C. Hafner and J. Voros, "In situ Sensing of Single Binding Events by Localized Surface Plasmon Resonance," Nano Lett. 8, 3450 (2008).

[2] F. Vollmer and S. Arnold, "Whispering-gallery-mode biosensing: label-free detection down to single molecules," Nat. Methods. 5, 591 (2008).

[3] A. J. Qavi, A. L. Washburn, J. Y. Byeon, and R. C. Bailey, "Label-free technologies for quantitative multiparameter biological analysis," Anal. and Bioanal. Chem. 394, 121 (2009).

[4] F. Vollmer, S. Arnold and D. Keng, "Single Virus detection from the reactive shift of a whispering-gallery mode," Proc. Natl. Acad. Sci. U.S.A. 105, 20701 (2008).

[5] A. Ramachandran, S. Wang, J. Clarke, S. J. Ja, D. Goad, L. Wald, E. M. Flood, E. Knobbe, J. V. Hryniewicz, S. T. Chu, D. Gill, W. Chen. O. King and B. E. Little, "A universal biosensing platform based on optical micro-ring resonators," Biosens. Bioelectron. 23, 939 (2008).

[6] A. M. Armani, R. P. Kulkarni, S. E. Fraser, R. C. Flagan and K. J. Vahala, "Label-free, single molecule detection with optical microcavities," Science 317, 783 (2007).

[7] L. Nogueira, R. Corradi and J. A. Eastham, "Prostate specific antigen for prostate cancer detection," Int. Braz. J. Urol. 35, 521 (2009).

[8] N. Satyan, A. Vasilyev, G. Rakuljic, V. Leyva and A. Yariv "Precisely controllable broadband frequency sweeps using a semiconductor laser in an optoelectronic phase-lock loop," Opt. Express 17, 15991 (2009).

[9] A. B. Matsko and V. S. Ilchenko, "Optical resonators with whispering-gallery modes—Part I: Basics," J. Sel. Top. Quantum Electron. 12, 3 (2006).

[10] V. S. Ilchenko A. B. Matsko, "Optical resonators with whispering-gallery modes—Part II: Applications," IEEE J. Sel. Top. Quantum Electron. 12, 15 (2006).

[11] F. Vollmer, D. Braun, A. Libchaber, M. Khoshsima, I. Teraoka and S. Arnold, "Protein detection by optical shift of a resonant microcavity." App. Phys. Lett. 80, 4057 (2002).

[12] I. S. Grudinin, V. S. Ilchenko and L. Maleki, "Ultrahigh optical Q factors of crystalline resonators in the linear regime," Phys. Rev. A 74, 063806 (2006).

[13] X. D. Fan, I. M. White, S. I. Shopoua, H. Y. Zhu, J. D. Suter and Y. Z. Sun, "Sensitive optical biosensors for unlabeled targets: A review," Anal. Chim. Acta 620, 8 (2008).

[14] George M. Hale and Marvin R. Querry. "Optical Constants of Water in the 200-nm to 200 μm Wavelength Region," Appl. Opt. 12, 555 (1973).

[15] L. Pang, G M Hwang, B Slutsky and Y Fainman, "Spectral sensitivity of two-dimensional nanohole array surface plasmon resonance sensor," App. Phys. Lett. 91, 123112 (2007).

[16]

[17]

[18] A. M. Armani and K. J. Vahala, "Heavy water detection using ultra-high-Q microcavities," Opt. Lett. 31, 1896 (2006)

[19] J. Kalia and R. T. Raines, "Advances in Bioconjugation," Curr. Org. Chem. 14, 138 (2010).

[20] P. Harder, M. Grunze, R. Dahint, G. M. Whitesides and P. E. Laibinis, "Molecular Conformation in Oligo (ethylene glycol)-Terminated Self-Assembled Monolayers on Gold and Silver Surfaces Determines Their Ability To Resist Protein Adsorption," J. Phys. Chem. B 102, 426 (1998).

[21] E. Ostuni, R. G. Chapman, R. E. Holmlin, S. Takayama, G. M. Whitesides, "A Survey of Structure—Property Relationships of Surfaces that Resist the Adsorption of Protein," Langmuir 17, 5605 (2001).

[22] A. Schlossbauer, D. Schaffert, J. Kecht, E. Wagner and T. Bein, "Click chemistry for high-density biofunctionalization of mesoporous silica," J. Am. Chem. Soc. 130, 12558 (2008).

[23] X. L. Sun, C. L. Stabler, C. S. Cazalis and E. L. Chaikof, "Carbohydrate and protein immobilization onto solid surfaces by sequential Diels-Alder and azide-alkyne cycloadditions," Bioconj. Chem. 17, 52 (2006).

[24] S. Tombelli, A. Minunni and A. Mascini, "Analytical applications of aptamers," Biosens. Bioelectron. 20, 2424 (2005).

[25] Almeida, V. R., R. R. Panepucci, and M. Lipson, Nanotaper for compact mode conversion. Optics Letters, 2003. 28(15): p. 1302-1304.

[26] McNab, S. J., N. Moll, and Y. A. Vlasov, Ultra-low loss photonic integrated circuit with membrane-type photonic crystal waveguides. Optics Express, 2003. 11(22): p. 2927-2939.

[27] Sun, X. K., H. C. Liu, and A. Yariv, Adiabaticity criterion and the shortest adiabatic mode transformer in a coupled-waveguide system. Optics Letters, 2009. 34(3): p. 280-282.

The invention claimed is:

1. A system for detecting and measuring biomolecules, comprising: an optoelectronic swept-frequency laser system for providing a coherent, swept-frequency optical input signal;

an optical resonator, surface-functionalized to bind to a target biomolecule and wherein resonance behavior of the resonator is adapted to change as a function of the binding of the target biomolecule;

an integrated waveguide for coupling the swept-frequency optical input signal to the optical resonator;

at least one external waveguide for coupling the swept-frequency optical input signal between the integrated waveguide and the optoelectronic swept-frequency laser system and between the integrated waveguide and a sensor photodetector;

a microfluidic cell for containing the optical resonator and delivering the target biomolecule to the optical resonator;

a sensor photodetector, for measuring a swept-frequency optical output signal from the optical waveguide, thus detecting changes in the resonance behavior of the resonator; and a signal processing unit for identifying the changes in resonance behavior, thus detecting and measuring biomolecules, wherein the optoelectronic swept-frequency laser system, comprises:

a semiconductor laser, wherein the semiconductor laser is adapted to emit a coherent optical signal and a frequency of the coherent optical signal is adjustable, in operation, by an injection current input to the semiconductor laser; and an optoelectronic feedback loop, coupled to the semiconductor laser, for providing, in operation, the injection current input based on the frequency of the coherent optical signal, wherein the optoelectronic feedback circuit comprises an optical portion and an electrical portion and wherein the optical portion comprises a signal divider, an interferometer, and a photodetector and the electrical portion comprises a reference oscillator, an electronic mixer, an integrator circuit and a summation circuit.

2. The system according to claim 1, wherein the optical resonator geometry is selected from the group consisting of substantially microtoroidal, substantially oblate spheroid, substantially spherical, substantially cylindrical, substantially disk-shaped, and substantially ring-shaped.

3. The system according to claim 1, wherein the optical resonator is a Bragg resonator.

4. The system according to claim 1, wherein the optical resonator comprises silicon nitride.

5. The system according to claim 1, wherein the optical resonator comprises silicon.

6. The system according to claim 1, wherein the optical resonator and the integrated waveguide are fabricated concurrently by microfabrication techniques.

7. A microfluidic flow system for detecting and measuring biomolecules, comprising:

an optoelectronic swept-frequency laser system for providing a coherent, swept-frequency optical input signal;

an optical resonator, surface-functionalized to bind to a target biomolecule and wherein resonance behavior of the resonator is adapted to change as a function of the binding of the target biomolecule;

an integrated waveguide, for coupling the swept-frequency optical input signal to the optical resonator;

a first external waveguide for coupling the swept-frequency optical input signal between the integrated waveguide and the optoelectronic swept-frequency laser system;

a fluid inlet for delivering a test fluid to the resonator, the test fluid may comprise the target molecule;

a fluid outlet for removing the test fluid from the resonator, the fluid may comprise the target molecule;

a sensor photodetector, for measuring a swept-frequency optical output signal from the first external waveguide, thus detecting changes in the resonance behavior of the resonator;

a second external waveguide for coupling between the integrated waveguide and the sensor photodetector; and a signal processing unit, for identifying the changes in resonance behavior, thus detecting and measuring biomolecules, wherein the optoelectronic swept-frequency laser system, comprises:

a semiconductor laser, wherein the semiconductor laser is adapted to emit a coherent optical signal and a frequency of the coherent optical signal is adjustable, in operation, by an injection current input to the semiconductor laser; and an optoelectronic feedback loop, coupled to the semiconductor laser, for providing, in operation, the injection current input based on the frequency of the coherent optical signal, wherein the optoelectronic feedback circuit comprises an optical portion and an electrical portion and wherein the optical portion comprises a signal divider, an interferometer, and a photodetector and the electrical portion comprises a reference oscillator, an electronic mixer, an integrator circuit and a summation circuit.

8. A method for fabricating a biomolecular sensor, comprising:

providing a substrate;

patterning a first set of features on the substrate utilizing microlithography, the first set of features comprising an optical resonator, an integrated waveguide, and portions of a microfluidic cell;

performing etch on the patterned substrate, thus forming the optical resonator, the integrated waveguide, and portions of the microfluidic cell;

depositing a second material;

patterning a first set of features on the substrate utilizing microlithography, the first set of features comprising a spot size converter and portions of the microfluidic cell;

performing etch on the patterned substrate, thus forming a spot size converter, and portions of the microfluidic cell; and coupling the integrated waveguide to an optoelectronic swept-frequency laser system and a sensor photodetector utilizing one or more external waveguides, wherein the sensor photodetector is coupled to a sensor processing unit; thus fabricating the biomolecular sensor, wherein the optoelectronic swept-frequency laser system, comprises:

a semiconductor laser, wherein the semiconductor laser is adapted to emit a coherent optical signal and a frequency of the coherent optical signal is adjustable, in operation, by an injection current input to the semiconductor laser; and an optoelectronic feedback loop, coupled to the semiconductor laser, for providing, in operation, the injection current input based on the frequency of the coherent optical signal, wherein the optoelectronic feedback circuit comprises an optical portion and an electrical portion and wherein the optical portion comprises a signal divider, an interferometer, and a photodetector and the electrical portion comprises a reference oscillator, an electronic mixer, an integrator circuit and a summation circuit.

9. A method for high-resolution 3-D imaging, comprising:

providing a swept-frequency optical signal utilizing an optoelectronic swept-frequency laser system;

scanning an imaging target to be imaged with the swept-frequency optical signal;

illuminating the imaging target with the swept-frequency optical signal, wherein the illuminating generates reflected light with time delay;

mixing the reflected light with the swept-frequency optical signal;

sending the mixed light to a photodetector and generating a photocurrent;

measuring frequency component of the photocurrent to generate measured distances; and mapping the measure distances as a function of the scan, thus generating a high-resolution 3-D image, wherein the optoelectronic swept-frequency laser system, comprises:

a semiconductor laser, wherein the semiconductor laser is adapted to emit a coherent optical signal and a frequency of the coherent optical signal is adjustable, in operation, by an injection current input to the semiconductor laser; and an optoelectronic feedback loop, coupled to the semiconductor laser, for providing, in operation, the injection current input based on the frequency of the coherent optical signal, wherein the optoelectronic feedback circuit comprises an optical portion and an electrical portion and wherein the optical portion comprises a signal divider, an interferometer, and a photodetector and the electrical portion comprises a reference oscillator, an electronic mixer, an integrator circuit and a summation circuit.

* * * * *